US012752119B2

(12) United States Patent
Prutchi et al.

(10) Patent No.: US 12,752,119 B2
(45) Date of Patent: Oct. 6, 2026

(54) INCREASING PEAK $VO_2$ IN PATIENTS WITH HF USING CARDIAC CONTRACTILITY MODULATION STIMULATION

(71) Applicant: Impulse Dynamics NV, Willemstad (CW)

(72) Inventors: David Prutchi, Voorhees, NJ (US); Simeon Ioannis Kedikoglou, Tallahassee, FL (US); Angela Connolly Stagg, Allendale, NJ (US)

(73) Assignee: Impulse Dynamics NV, Willemstad (CW)

( * ) Notice: Subject to any disclaimer, the term of this patent is extended or adjusted under 35 U.S.C. 154(b) by 913 days.

(21) Appl. No.: 17/770,318

(22) PCT Filed: Oct. 22, 2020

(86) PCT No.: PCT/IB2020/059943
§ 371 (c)(1),
(2) Date: Apr. 20, 2022

(87) PCT Pub. No.: WO2021/079316
PCT Pub. Date: Apr. 29, 2021

(65) Prior Publication Data
US 2022/0387790 A1 Dec. 8, 2022

Related U.S. Application Data

(60) Provisional application No. 62/924,782, filed on Oct. 23, 2019, provisional application No. 62/924,776, filed on Oct. 23, 2019.

(51) Int. Cl.
*A61B 5/369* (2021.01)
*A61N 1/362* (2006.01)

(52) U.S. Cl.
CPC .................................... *A61N 1/362* (2013.01)

(58) Field of Classification Search
CPC ......... A61N 1/362; A61N 1/369; A61N 1/372
(Continued)

(56) References Cited

U.S. PATENT DOCUMENTS 4,554,922 A 11/1985 Prystowsky et al.
5,372,607 A 12/1994 Stone et al.
(Continued)

FOREIGN PATENT DOCUMENTS

CA 2459408 3/2003
CN 1787850 6/2006
(Continued)

OTHER PUBLICATIONS

Abraham et al., A Randomized Controlled Trial to Evaluate the Safety and Efficacy of Cardiac Contractility Modulation, Oct. 2018, Elsevier, pp. 1-9.*
(Continued)

*Primary Examiner* — Nicole F Johnson

(57) ABSTRACT

A method of increasing peak VO2 including selecting a patient having impaired peak VO2 and estimated to have a potential for improving peak VO2, and applying cardiac contractility modulation stimulation to the patient's heart. A method of increasing peak VO2 including detecting ventricle contraction using one or more leads in a patient's ventricle, and applying Cardiac Contractility Modulation stimulation to the patient's ventricle, after a delay from a time of the detecting, thereby increasing the patient's peak VO2. Related apparatus and methods are also described.

16 Claims, 8 Drawing Sheets

(58) Field of Classification Search
USPC .............................................................. 607/9
See application file for complete search history.

(56) References Cited

U.S. PATENT DOCUMENTS

| | | | |
|---|---|---|---|
| 6,233,487 | B1 | 5/2001 | Mika et al. |
| 6,263,242 | B1 | 7/2001 | Mika et al. |
| 6,370,430 | B1 | 4/2002 | Mika et al. |
| 6,480,737 | B1 | 11/2002 | Policker et al. |
| 6,597,952 | B1 | 7/2003 | Mika et al. |
| 6,725,093 | B1 | 4/2004 | Ben-Haim et al. |
| 6,993,385 | B1 | 1/2006 | Routh et al. |
| 7,027,863 | B1 | 4/2006 | Prutchi et al. |
| 7,519,426 | B1 | 4/2009 | Koh et al. |
| 7,634,310 | B2 | 12/2009 | Lee et al. |
| 7,953,481 | B1 | 5/2011 | Shemer et al. |
| 7,991,469 | B2 | 8/2011 | Schwartz et al. |
| 8,594,788 | B2 | 11/2013 | Weiss et al. |
| 8,634,910 | B2 | 1/2014 | Stahmann |
| 8,977,353 | B2 | 3/2015 | Rousso et al. |
| 9,713,723 | B2 | 7/2017 | Shemer et al. |
| 10,207,110 | B1 | 2/2019 | Gelfand et al. |
| 2003/0036777 | A1 | 2/2003 | Sheth et al. |
| 2004/0127804 | A1 | 7/2004 | Hatlesad et al. |
| 2005/0039745 | A1 | 2/2005 | Stahmann et al. |
| 2005/0085867 | A1 | 4/2005 | Tehrani et al. |
| 2005/0090871 | A1 | 4/2005 | Cho et al. |
| 2005/0142070 | A1* | 6/2005 | Hartley ................ A61B 5/4818 604/890.1 |
| 2006/0100668 | A1 | 5/2006 | Ben-David et al. |
| 2006/0224190 | A1 | 10/2006 | Gill et al. |
| 2007/0060962 | A1 | 3/2007 | Pappone |
| 2008/0021336 | A1 | 1/2008 | Dobak, III |
| 2008/0103532 | A1 | 5/2008 | Armstrong et al. |
| 2008/0114411 | A1 | 5/2008 | Lian et al. |
| 2008/0275520 | A1 | 11/2008 | Hopper et al. |
| 2008/0319500 | A1 | 12/2008 | Zhu et al. |
| 2009/0030471 | A1 | 1/2009 | Rousso et al. |
| 2009/0062882 | A1 | 3/2009 | Zhang et al. |
| 2009/0248101 | A1 | 10/2009 | Anker |
| 2009/0287103 | A1 | 11/2009 | Pillai |
| 2010/0069977 | A1 | 3/2010 | Stahmann |
| 2010/0069985 | A1* | 3/2010 | Stahmann .......... A61N 1/36185 607/9 |
| 2010/0087892 | A1 | 4/2010 | Stubbs et al. |
| 2010/0248288 | A1 | 9/2010 | I Iess et al. |
| 2010/0305647 | A1 | 12/2010 | McCabe et al. |
| 2011/0152956 | A1 | 6/2011 | Hincapie-Ordonez et al. |
| 2013/0006319 | A1 | 1/2013 | Doerr |
| 2013/0138006 | A1 | 5/2013 | Bornzin et al. |
| 2013/0218222 | A1 | 8/2013 | Doerr |
| 2016/0045732 | A1 | 2/2016 | Grenz et al. |
| 2017/0245794 | A1 | 8/2017 | Sharma et al. |
| 2017/0348524 | A1 | 12/2017 | Matos |
| 2018/0214698 | A1 | 8/2018 | Cuchiara et al. |
| 2019/0060632 | A1 | 2/2019 | Asirvatham et al. |
| 2019/0329043 | A1 | 10/2019 | Sharma |
| 2019/0329052 | A1 | 10/2019 | Kim et al. |
| 2022/0379120 | A1 | 12/2022 | Prutchi et al. |
| 2022/0387795 | A1 | 12/2022 | Prutchi et al. |
| 2023/0001204 | A1 | 1/2023 | Prutchi et al. |
| 2023/0173280 | A1 | 6/2023 | Prutchi et al. |

FOREIGN PATENT DOCUMENTS

| | | |
|---|---|---|
| CN | 1882296 | 12/2006 |
| CN | 101827629 | 9/2010 |
| CN | 104321107 | 1/2015 |
| CN | 107261324 | 10/2017 |
| EP | 0334675 | 9/1989 |
| EP | 0600631 | 6/1994 |
| EP | 0910429 | 4/1999 |
| EP | 2659931 | 11/2013 |
| JP | 2007-503286 | 2/2007 |
| JP | 2008-532630 | 8/2008 |
| JP | 2010-104750 | 5/2010 |
| JP | 2011-502552 | 1/2011 |
| JP | 2012-502729 | 2/2012 |
| JP | 2012-504468 | 2/2012 |
| JP | 2015-503397 | 2/2015 |
| WO | WO 2004/080533 | 9/2004 |
| WO | WO 2010/039877 | 4/2010 |
| WO | WO 2021/079316 | 4/2021 |
| WO | WO 2021/079318 | 4/2021 |
| WO | WO 2021/079319 | 4/2021 |
| WO | WO 2021/198755 | 10/2021 |

OTHER PUBLICATIONS

Official Action Dated Sep. 8, 2023 from the US Patent and Trademark Office Re. U.S. Appl. No. 17/857,085. (24 pages).
Eisman et al. "Pulmonary Capillary Wedge Pressure Patterns During Exercice Predict Exercise Capacity and Incident Heart Failure", Circulation: Heart Failure, 11(5): 1-9, May 2018.
Meluzin et al. "Improvement in The Prediction of Exercise-Induced Elevation of Left Ventricular Filling Pressure in Patients With Normal Left Ventricular Ejection Fraction", Echocardiography, 34(1): 78-86, Oct. 25, 2016. Abstract.
Notice of Reason(s) for Rejection Dated Jun. 6, 2024 From the Japan Patent Office Re. Application No. 2022-523513 and Its Translation Into English. (12 Pages).
Notice of Reason(s) for Rejection Dated May 28, 2024 From the Japan Patent Office Re. Application No. 2022-523514 and Its Translation Into English. (14 Pages).
Interview Summary Dated Nov. 12, 2024 from the US Patent and Trademark Office Re. U.S. Appl. No. 17/857,085. (8 pages).
Notice of Reason(s) for Rejection Dated Mar. 4, 2025 From the Japan Patent Office Re. Application No. 2022-523514 and Its Translation Into English. (12 Pages).
Notice of Reason(s) for Rejection Dated Feb. 12, 2025 From the Japan Patent Office Re. Application No. 2022-523998 and Its Translation Into English. (9 Pages).
Official Action Dated Feb. 6, 2025 from the US Patent and Trademark Office Re. U.S. Appl. No. 17/911,676. (48 pages).
Restriction Official Action Dated Jan. 6, 2025 from the US Patent and Trademark Office Re. U.S. Appl. No. 17/770,707. (12 pages).
Oliver et al. "Anatomy, Thorax, Phrenic Nerves", Europe PMC, Search life-sciences literature, Study Guide from StatPearls Publishing, Treasure Island (FL), PMID: 30020697, Jul. 19, 2018. dowloaded from https://europepmc.org/article/nbk/nbk513325.
Additional Search Fees Due under Rule 164(2)(a) EPC Dated Feb. 26, 2025 From the European Patent Office Re. Application No. 20803263.1 (5 pages).
Interview Summary Dated Mar. 21, 2025 from the US Patent and Trademark Office Re. U.S. Appl. No. 17/770,329. (8 pages).
Notification of Office Action and Search Report Dated Apr. 1, 2025 From the State Intellectual Property Office of the People's Republic of China Re. Application No. 202080089348.6 and Its Machine Translation of Office Action into English. (10 Pages).
Notification of Office Action and Search Report Dated Mar. 19, 2025 From the State Intellectual Property Office of the People's Republic of China Re. Application No. 202080088570.4 and its Translation of the Office Action into English. (30 Pages).
Notification of Office Action and Search report Dated Mar. 21, 2025 From the State Intellectual Property Office of the People's Republic of China Re. Application No. 202080090192.3 and Its Translation in English (18 Pages).
Notification of Office Action and Search Report Dated Mar. 26, 2025 From the State Intellectual Property Office of the People's Republic of China Re. Application No. 202080101268.8 and Its Machine Translation of Office Action into English. (26 Pages).
Communication Pursuant to Article 94(3) EPC Dated Dec. 22, 2023 From the European Patent Office Re. Application No. 20801017.3 (4 Pages).
El Shear "Novel Paradigms in the Therapeutic Management of Heart Failure With Preserved Ejection Fraction: Clinical Perspectives", American Journal of Cardiovascular Disease, 9(5): 91-108, Oct. 15, 2019.

(56) References Cited

OTHER PUBLICATIONS

Tschöpe et al. "Cardiac Contractility Modulation Signals Improve Exercise Intolerance and Maladaptive Regulation of Cardiac Key Proteins for Systolic and Diastolic Function in HFpEF", International Journal of Cardiology, 203: 1061-1066, Available Online Oct. 27, 2015.
Zile et al. "New Concepts in Diastolic Dysfunction and Diastolic Heart Failure: Part I. Diagnosis, Prognosis, and Measurements of Diastolic Function", Circulation, 105(11): 1387-1393, Mar. 19, 2002.
Zile et al. "New Concepts in Diastolic Dysfunction and Diastolic Heart Failure: Part II. Causal Mechanisms and Treatment", Circulation, 105(12): 1503-1508, Mar. 26, 2002.
Official Action Dated Oct. 11, 2024 from the US Patent and Trademark Office Re. U.S. Appl. No. 17/770,329. (26 pages).
Notice of Reason(s) for Rejection Dated Jun. 11, 2024 From the Japan Patent Office Re. Application No. 2022-523998 and Its Translation Into English. (10 Pages).
Official Action Dated Aug. 5, 2024 from the US Patent and Trademark Office Re. U.S. Appl. No. 17/857,085. (21 pages).
Cleveland Clinic "Hypertrophic Cardiomyopathy", Cleveland Clinic, Retrieved Online, pp. 1-2, 2021.
Meluzin et al. "Noninvasive Prediction of the Exercise-Induced Elevation in Left Ventricular Filling Pressure in Post-Heart Transplant Patients With Normal Left Ventricular Ejection Fraction", Clinical Cardiology, 18(2): 63-72, 2013.
Notice of Reasons for Rejection Dated Dec. 3, 2024 From the Japan Patent Office Re. Application No. 2022-523513 and Its Translation into English. (12 Pages).
Official Action Dated Jan. 17, 2024 from the US Patent and Trademark Office Re. U.S. Appl. No. 17/857,085. (11 pages).
English Translation Dated May 7, 2025 of Notification of Office Action and Search Report Dated Apr. 1, 2025 From the State Intellectual Property Office of the People's Republic of China Re. Application No. 202080089348.6 and Its Machine Translation of Office Action into English. (6 Pages).
Official Action Dated Mar. 20, 2024 from the US Patent and Trademark Office Re. U.S. Appl. No. 17/770,329. (39 pages).
International Search Report and the Written Opinion Dated Feb. 4, 2021 From the International Searching Authority Re. Application No. PCT/IB2020/059949. (14 Pages).
International Search Report and the Written Opinion Dated Aug. 12, 2021 From the International Searching Authority Re. Application No. PCT/IB2020/059947. (16 Pages).
International Search Report and the Written Opinion Dated Jan. 14, 2021 From the International Searching Authority Re. Application No. PCT/IB2020/059943. (17 Pages).
International Search Report and the Written Opinion Dated Aug. 20, 2021 From the International Searching Authority Re. Application No. PCT/IB2020/059944. (18 Pages).
Invitation to Pay Additional Fees, Communication Relating to the Result of the Partial International Search and the Provisional Opinion Dated Apr. 20, 2021 From the International Searching Authority Re. Application No. PCT/IB2020/059944. (9 Pages).
Invitation to Pay Additional Fees, Communication Relating to the Result of the Partial International Search and the Provisional Opinion Dated Apr. 26, 2021 From the International Searching Authority Re. Application No. PCT/IB2020/059947. (9 Pages).
Written Opinion Dated Mar. 15, 2022 From the International Searching Authority Re. Application No. PCT/IB2020/059944. (9 Pages).
Abi-Samra et al. "Cardiac Contractility Modulation: A Novel Approach for the Treatment of Heart Failure", Heart Fail Reviews 21:645-660, Jul. 9, 2016.
Abraham et al. "A Randomized Controlled Trial to Evaluate the Safety and Efficacy of Cardiac Contractility Modulation in Patients With Moderately Reduced Left Ventricular Ejection Fraction and A Narrow QRS Duration: Study Rationale and Design", Journal of Cardiac Failure, 21(1): 16-23, Jan. 2015.
Abraham et al. "A Randomized Controlled Trial to Evaluate the Safety and Efficacy of Cardiac Contractility Modulation", Journal of the American College of Cardiology, JACC: Heart Failure, 6(10): 874-883, Published Online May 10, 2018.
Abraham et al. "Subgroup Analysis of A Randomized Controlled Trial Evaluating the Safety and Efficacy of Cardiac Contractility Modulation in Advanced Heart Failure", Journal of Cardiac Failure, 17(9): 710-717, Published Online Jun. 22, 2011.
Anker et al. "Cardiac Contractility Modulation Improves Long-Term Survival and Hospitalizations in Heart Failure With Reduced Ejection Fraction", European Journal of Heart Failure, 21(9): 1103-1113, Published Online Jan. 16, 2019.
Borggrefe et al. "Randomized, Double Blind Study of Non-Excitatory, Cardiac Contractility Modulation Electrical Impulses for Symptomatic Heart Failure", European Heart Journal, 29(8): 1019-1028, Published Online Feb. 12, 2008.
Giallauria et al. "Effects of Cardiac Contractility Modulation by Non-Excitatory Electrical Simulation on Exercise Capacity and Quality of Life: An Individual Patient's Data Meta-Analysis of Randomized Controlled Trials", International Journal of Cardiology, XP028880522, 175(2): 352-357, Available Online Jun. 19, 2014.
Ibrahim et al. "Power Prior Distributions for Regression Models", Statistical Science, 15(1): 46-60, Feb. 2000.
Kadish et al. "A Randomized Controlled Trial Evaluating the Safety and Efficacy of Cardiac Contractility Modulation in Advanced Heart Failure", American Heart Journal, 161(2): 329-337, Feb. 2011.
Kuschyk et al. "Efficacy and Survival in Patients With Cardiac Contractility Modulation: Long-Term Single Center Experience in 81 Patients", International Journal of Cardiology, 183: 76-81, Available Online Jan. 20, 2015.
Liu et al. "Improvement of Long-Term Survival by Cardiac Contractility Modulation in Heart Failure Patients: A Case-Control Study", International Journal of Cardiology, 206: 122-126, Available On line Jan. 6, 2016.
Lyon et al. "Cardiac Contractility Modulation Therapy in Advanced Systolic Heart Failure", Nature Reviews Cardiology, XP0557621686, 10(10): 584-598, Advance Online Publication Aug. 13, 2013.
Mando et al. "Outcomes of Cardiac Contractility Modulation: A Systemic Review and Meta-Analysis of Randomized Clinical Trials", Cardiovascular Therapeutics, 2019(Art.ID 9769724): 1-10, Jun. 17, 2019.
Mueller et al. "Clinical Effects of Long-Term Cardiac Contractility Modulation (CCM) in Subjects With Heart Failure Caused by Left Ventricular Systolic Dysfunction", Clinical Research of Cardiology, 106(11): 893-904, Published Online Jul. 6, 2017.
Neelagaru et al. "Nonexcitatory, Cardiac Contractility Modulation Electrical Impulses: Feasibility Study for Advanced Heart Failure in Patients With Normal QRS Duration", Heart Rythm, 3(10): 1140-1147, Published Online Jul. 8, 2006.
Schoene et al. "Cardiac Contractility Modulation Provides Improved Ventilatory Efficiency and Reduces Oscillatory Breathing Pattern", European Heart Journal, Poster Session 4: Advanced Heart Failure, 40(Suppl.1): 2133: # p. 3523, Oct. 21, 2019.
Schuirmann "Pharmacometrics: A Comparison of the Two One-Sided Tests Procedure and the Power Approach for Assessing the Equivalence of Average Bioavailability", Journal of Pharmacokinetics and Biopharmaceutics, 15(6): 657- 680, Dec. 1987.
Tint et al. "New Generation Cardiac Contractility Modulation Device—Filling the Gap in Heart Failure Treatment", Journal of Clinical Medicine, 8(5): 588-1-588-10, Apr. 29, 2019.
Tschoepe et al. "Cardiac Contractility Modulation: Mechanisms of Action in Heart Failure with Reduced Ejection Fraction and Beyond", European Journal of Heart Failure, 21(1):14-20, Nov. 28, 2018.
Uskach et al. "Possibilities and Perspectives of Using Cardiac Contractility Modulation in Patients With Chronic Heart Failure and Atrial Fibrillation", Kardiologiia, 59(2S): 4-14, 2019 & English Abstract.
Wang et al. "Meta-Analysis of the Incidence of Lead Dislodgement With Conventional and Leadless Pacemaker Systems", Pacing and Clinical Electrophysiology, PACE, 41(10): 1365-1371, Published Online Aug. 27, 2018.

(56) References Cited

OTHER PUBLICATIONS

Yu et al. "Impact of Cardiac Contractility Modulation on Left Ventricular Global and Regional Function and Remodeling", Journal of the American College of Cardiology, JACC: Cardiovascular Imaging, 2(12): 1341-1349, Dec. 2009.
International Preliminary Report on Patentability Dated May 5, 2022 From the International Bureau of WIPO Re. Application No. PCT/IB2020/059943. (8 Pages).
International Preliminary Report on Patentability Dated May 5, 2022 From the International Bureau of WIPO Re. Application No. PCT/IB2020/059947. (10 Pages).
International Preliminary Report on Patentability Dated May 5, 2022 From the International Bureau of WIPO Re. Application No. PCT/IB2020/059949. (10 Pages).
Notice of Reasons for Rejection Dated Jul. 15, 2025 From the Japan Patent Office Re Application No. 2022-523998 and its Translation into English. (6 Pages).
Communication Pursuant to Rule 164(2)(b) and Article 94(3) EPC Dated Jun. 11, 2025 From the European Patent Office Re. Application No. 20803263.1 (11 Pages).
Notification of Office Action and Search Report Dated Dec. 17, 2025 From the State Intellectual Property Office of the People's Republic of China Re. Application No. 202080089348.6 and Its Machine Translation of Office Action into English. (12 Pages).
Pre Appeal Examination Dated Feb. 17, 2026 From the Japan Patent Office Re. Application No. 2022-523998 and Its Translation Into English. (6 Pages).
International Preliminary Report on Patentability Dated Jul. 21, 2022 From the International Preliminary Examining Authority Re. Application No. PCT/IB2020/059944. (21 Pages).
Notification of Office Action Dated May 14, 2026 From the National Intellectual Property Administration of the People's Republic of China Re. Application No. 202080089348.6 and Its Machine Translation Into English. (16 Pages).

* cited by examiner

INCREASING PEAK $VO_2$ IN PATIENTS WITH HF USING CARDIAC CONTRACTILITY MODULATION STIMULATION

RELATED APPLICATIONS

This application is a National Phase of PCT Patent Application No. PCT/IB2020/059943 having International filing date of Oct. 22, 2020, which claims the benefit of priority under 35 USC 119 (e) of U.S. Provisional Patent Application Nos. 62/924,782 and 62/924,776, both filed on Oct. 23, 2019.

PCT Patent Application No. PCT/IB2020/059943 is part of a co-filing of the following PCT applications, all filed on Oct. 22, 2020 and by the same applicant, Impulse Dynamics NV:

PCT Patent Application No. PCT/IB2020/059949, titled "CARDIAC CONTRACTILITY MODULATION FOR ATRIAL ARRHYTHMIA PATIENTS";

PCT Patent Application No. PCT/IB2020/059947, titled "METHODS FOR PLANNING AND DELIVERING CARDIAC ELECTRICAL STIMULATION"; and PCT Patent Application No. PCT/IB2020/059944, titled "CARDIAC CONTRACTILITY MODULATION IN ASSOCIATION WITH RESPIRATION".

The contents of the above applications are all incorporated by reference as if fully set forth herein in their entirety.

FIELD AND BACKGROUND OF THE INVENTION

The present invention, in some embodiments thereof, relates to using cardiac contractility modulation stimulation to increase Peak $VO_2$ in patients.

Cardiac Contractility Modulation treatment is delivered by an implanted device that applies non-excitatory electrical signals NES, adjusted to and synchronized with electrical action in the cardiac cycle. Other than a pacemaker, which delivers an electrical signal with the intention to result in cardiac contraction, the Cardiac Contractility Modulation treatment applies the NES, adjusted to and synchronized with electrical action in the cardiac cycle.

In Cardiac Contractility Modulation therapy, electrical stimulation is applied to the cardiac muscle during an absolute refractory period. In this phase of the cardiac cycle, electrical signals do not trigger new cardiac muscle contractions, hence this type of stimulation is known as a non-excitatory stimulation (NES).

Additional background art includes:

U.S. Pat. No. 6,480,737 titled "Field Delivery Safety System Using Detection of Atypical ECG".

U.S. Pat. No. 9,713,723 titled "Signal Delivery through the Right Ventricular Septum".

U.S. Pat. No. 4,554,922, apparently suggests that electrical signals applied in the relative refractory period extend the refractory period and make tissue less pro-arrhythmic.

1. Lyon A R, Samara M A and Feldman D S. Cardiac contractility modulation therapy in advanced systolic heart failure. *Nat Rev Cardiol.* 2013; 10:584-98.
2. Tschope C, Kherad B, Klein O, Lipp A, Blaschke F, Gutterman D, Burkhoff D, Hamdani N, Spillmann F and Van Linthout S. Cardiac contractility modulation: mechanisms of action in heart failure with reduced ejection fraction and beyond. *Eur J Heart Fail.* 2019; 21:14-22.
3. Borggrefe M M, Lawo T, Butter C, Schmidinger H, Lunati M, Pieske B, Misier A R, Curnis A, Bocker D, Remppis A, Kautzner J, Stuhlinger M, Leclerq C, Taborsky M, Frigerio M, Parides M, Burkhoff D and Hindricks G. Randomized, double blind study of non-excitatory, cardiac contractility modulation electrical impulses for symptomatic heart failure. *Eur Heart J.* 2008; 29:1019-1028.
4. Neelagaru S B, Sanchez J E, Lau S K, Greenberg S M, Raval N Y, Worley S, Kalman J, Merliss A D, Krueger S, Wood M, Wish M, Burkhoff D and Nademanee K. Non-excitatory, cardiac contractility modulation electrical impulses: Feasibility study for advanced heart failure in patients with normal QRS duration. *Heart Rhythm.* 2006; 3:1140-1147.
5. Kadish A, Nademanee K, Volosin K, Krueger S, Neelagaru S, Raval N, Obel O, Weiner S, Wish M, Carson P, Ellenbogen K, Bourge R, Parides M, Chiacchierini R P, Goldsmith R, Goldstein S, Mika Y, Burkhoff D and Abraham W T. A randomized controlled trial evaluating the safety and efficacy of cardiac contractility modulation in advanced heart failure. *Am Heart J.* 2011; 161:329-337 e1-2.
6. Abraham W T, Nademanee K, Volosin K, Krueger S, Neelagaru S, Raval N, Obel O, Weiner S, Wish M, Carson P, Ellenbogen K, Bourge R, Parides M, Chiacchierini R P, Goldsmith R, Goldstein S, Mika Y, Burkhoff D and Kadish A. Subgroup analysis of a randomized controlled trial evaluating the safety and efficacy of cardiac contractility modulation in advanced heart failure. *J Card Fail.* 2011; 17:710-717.
7. Abraham W T, Kuck K H, Goldsmith R L, Lindenfeld J, Reddy V Y, Carson P E, Mann D L, Saville B, Parise H, Chan R, Wiegn P, Hastings J L, Kaplan A J, Edelmann F, Luthje L, Kahwash R, Tomassoni G F, Gutterman D D, Stagg A, Burkhoff D and Hasenfuss G. A Randomized Controlled Trial to Evaluate the Safety and Efficacy of Cardiac Contractility Modulation. *JACC Heart Fail.* 2018; 6:874-883.
8. Yu C M, Chan J Y, Zhang Q, Yip G W, Lam Y Y, Chan A, Burkhoff D, Lee P W and Fung J W. Impact of cardiac contractility modulation on left ventricular global and regional function and remodeling. *JACC Cardiovasc Imaging.* 2009; 2:1341-1349.
9. Kuschyk J, Roeger S, Schneider R, Streitner F, Stach K, Rudic B, Weiss C, Schimpf R, Papavasilliu T, Rousso B, Burkhoff D and Borggrefe M. Efficacy and survival in patients with cardiac contractility modulation: long-term single center experience in 81 patients. *Int J Cardiol.* 2015; 183:76-81.
10. Muller D, Remppis A, Schauerte P, Schmidt-Schweda S, Burkhoff D, Rousso B, Gutterman D, Senges J, Hindricks G and Kuck K H. Clinical effects of long-term cardiac contractility modulation (CCM) in subjects with heart failure caused by left ventricular systolic dysfunction. *Clin Res Cardiol.* 2017; 106:893-904.
11. Anker S D, Borggrefe M, Neuser H, Ohlow M A, Roger S, Goette A, Remppis B A, Kuck K H, Najarian K B, Gutterman D D, Rousso B, Burkhoff D and Hasenfuss G. Cardiac contractility modulation improves long-term survival and hospitalizations in heart failure with reduced ejection fraction. *Eur J Heart Fail.* 2019.
12. Liu M, Fang F, Luo X X, Ben Haim S, Burkhoff D, Chan J Y, Chan C P, Cheung L, Rousso B, Gutterman D and Yu C M. Improvement of long-term survival by cardiac contractility modulation in heart failure patients: A case-control study. *Int J Cardiol.* 2016; 206:122-126.
13. Wang Y, Hou W, Zhou C, Yin Y, Lu S, Liu G, Duan C, Cao M, Li M, Toft E S and Zhang H J. Meta-analysis of the incidence of lead dislodgement with conventional and leadless pacemaker systems. *Pacing Clin Electrophysiol.* 2018; 41:1365-1371.

14. Ibrahim J G and Chen M H. Power prior distributions for regression models. *Statist Sci.* 2000; 15:46-60.
15. Schuirmann D J. A comparison of the two one-sided tests procedure and the power approach for assessing the equivalence of average bioavailability. *J Pharmacokinet Biopharm.* 1987; 15:657-80.

The disclosures of all references mentioned above and throughout the present specification, as well as the disclosures of all references mentioned in those references, are hereby incorporated herein by reference.

SUMMARY OF THE INVENTION

The present invention, in some embodiments thereof, relates to using cardiac contractility modulation stimulation to increase Peak $VO_2$ in patients.

Some aspects of the invention include: selecting patients suitable for Cardiac Contractility Modulation stimulation to increase their Peak $VO_2$;

using Cardiac Contractility Modulation stimulation on patients to increase their Peak $VO_2$;

using a Cardiac Contractility Modulation with just two leads; It is noted that a potential benefit of a reduction of a number of leads, and specifically a reduction of an atrial lead, is having less leads in the veins;

using input sensing just from the heart ventricle; and using input sensing from just one or two leads to determine when to apply Cardiac Contractility Modulation stimulation.

According to an aspect of some embodiments of the present disclosure there is provided a method of planning Cardiac Contractility Modulation treatment for a patient to increase peak VO2, the method including selecting a patient having impaired peak VO2 and estimated to have a potential for improving peak VO2, and planning Cardiac Contractility Modulation Treatment for the patient.

According to some embodiments of the disclosure, the selecting includes selecting a patient who already has an implant suitable for providing Cardiac Contractility Modulation treatment.

According to some embodiments of the disclosure, the selecting include selecting a patient not known to have another medical condition which may prevent increasing peak VO2.

According to some embodiments of the disclosure, the selecting include selecting a patient estimated to have a pulmonary reserve.

According to some embodiments of the disclosure, the selecting the patient includes selecting a patient with a peak VO2 value below 25 ml $O_2$/min/kg.

According to some embodiments of the disclosure, the selecting the patient includes selecting a patient with a peak VO2 value below 20 ml $O_2$/min/kg.

According to some embodiments of the disclosure, the selecting the patient includes selecting a patient with a peak VO2 value above 5 ml $O_2$/min/kg.

According to some embodiments of the disclosure, the selecting the patient includes selecting a patient with a peak $VO_2$ value above 9 ml $O_2$/min/kg.

According to some embodiments of the disclosure, the selecting the patient includes selecting a patient with a NYHA class selected from a group consisting of NYHA class II, NYHA class III, and NYHA class IVa.

According to some embodiments of the disclosure, the selecting the patient includes selecting a patient with at least one pulmonary status selected from a group consisting of a Breathing Reserve (BR) above 30%, an Oxygen Uptake Efficiency Slope (OUES) below 90%, a peak RER above 1.05, VE/$VCO_2$ ratio above 30, and $O_2$ saturation not falling rapidly during exercise, for example, falling less than 10% over a period of 20 minutes of exercise.

According to some embodiments of the disclosure, the selecting the patient includes selecting a patient with an ejection fraction above 25% and below 50%.

According to some embodiments of the disclosure, the selecting the patient includes selecting a patient with an ejection fraction above 35% and below 45%.

According to some embodiments of the disclosure, the selecting the patient includes selecting a patient with heart failure.

According to some embodiments of the disclosure, the selecting the patient includes selecting a patient with at least one condition selected from a group consisting of atrial fibrillation (AF), Systolic heart failure (HF), Diastolic HF, Atrial Tachycardia, Angina, Myocarditis, Small vessel disease, Pulmonary hypertension, Chronic Obstructive Pulmonary Disease (COPD), and Sleep Apnea.

According to some embodiments of the disclosure, the planning includes planning a treatment which combines providing Cardiac Contractility Modulation Treatment with an additional cardiac treatment.

According to some embodiments of the disclosure, the selecting the patient includes selecting a patient having impaired peak VO2 and not known to have another medical condition which may limit increasing peak VO2 includes selecting a patient which is not known to have a condition selected from a group consisting of a limitation in pulmonary intake of oxygen, lung disease, a limitation in blood flow, and peripheral blood vessel disease.

According to some embodiments of the disclosure, further including detecting an improper beat when a difference between a first ventricle lead detecting ventricle contraction and a second ventricle lead detecting ventricle contraction is greater than 30 milliseconds, and not planning Cardiac Contractility Modulation stimulation application.

According to an aspect of some embodiments of the present invention there is provided a method of increasing peak $VO_2$ including selecting a patient having impaired peak $VO_2$ and estimated to have a potential for improving peak VO2, and applying Cardiac Contractility Modulation stimulation to the patient's heart.

According to some embodiments of the invention, the selecting include selecting a patient not known to have another medical condition which may prevent increasing peak VO2.

According to some embodiments of the invention, the selecting include selecting a patient estimated to have a pulmonary reserve.

According to some embodiments of the invention, the selecting the patient includes selecting a patient with a peak VO2 value below 25 ml $O_2$/min/kg. According to some embodiments of the invention, the selecting the patient includes selecting a patient with a peak $VO_2$ value below 20 ml $O_2$/min/kg.

According to some embodiments of the invention, the selecting the patient includes selecting a patient with a peak VO2 value above 5 ml $O_2$/min/kg. According to some embodiments of the invention, the selecting the patient includes selecting a patient with a peak VO2 value above 9 ml $O_2$/min/kg.

According to some embodiments of the invention, the selecting the patient includes selecting a patient with a NYHA class selected from a group consisting of NYHA class II, NYHA class III, and NYHA class IVa.

According to some embodiments of the invention, the selecting the patient includes selecting a patient with at least one pulmonary status selected from a group consisting of a Breathing Reserve (BR) above 30%, an Oxygen Uptake Efficiency Slope (OUES) below 90%, a peak RER above 1.05, VE/VCO2 ratio above 30, and O2 saturation not falling rapidly during exercise, for example, falling less than 10% over a period of 20 minutes of exercise.

According to some embodiments of the invention, the selecting the patient includes selecting a patient with an ejection fraction above 25% and below 50%. According to some embodiments of the invention, the selecting the patient includes selecting a patient with an ejection fraction above 35% and below 45%.

According to some embodiments of the invention, the selecting the patient includes selecting a patient with heart failure.

According to some embodiments of the invention, the selecting the patient includes selecting a patient with at least one condition selected from a group consisting of atrial fibrillation (AF), Systolic heart failure (HF), Diastolic HF, Atrial Tachycardia, Angina, Myocarditis, Small vessel disease, Pulmonary hypertension, Chronic Obstructive Pulmonary Disease (COPD), and Sleep Apnea.

According to some embodiments of the invention, the selecting the patient includes selecting a patient having impaired peak VO2 and not known to have another medical condition which may limit increasing peak VO2 includes selecting a patient which is not known to have a condition selected from a group consisting of a limitation in pulmonary intake of oxygen, lung disease, a limitation in blood flow, and peripheral blood vessel disease.

According to some embodiments of the invention, the applying Cardiac Contractility Modulation stimulation to the patient's heart includes using two leads to apply the Cardiac Contractility Modulation stimulation.

According to some embodiments of the invention, the applying Cardiac Contractility Modulation stimulation to the patient's heart includes using three leads to apply the Cardiac Contractility Modulation stimulation.

According to some embodiments of the invention, the applying Cardiac Contractility Modulation stimulation to the patient's heart includes using at least one lead including two electrodes.

According to some embodiments of the invention, the applying Cardiac Contractility Modulation stimulation to the patient's heart includes using at least one lead including at least one bipolar electrode.

According to some embodiments of the invention, the applying Cardiac Contractility Modulation stimulation to the patient's heart includes using one or more leads placed at locations selected from a group consisting of the ventricular septum, the right ventricle, the left ventricle, one location in the right ventricle and one location in the left ventricle.

According to some embodiments of the invention, the applying Cardiac Contractility Modulation stimulation to the patient's heart includes using two leads placed at ventricular walls.

According to some embodiments of the invention, further including implanting a Cardiac Contractility Modulation device and leads in the selected patient.

According to some embodiments of the invention, further including detecting an improper beat when a difference between a first ventricle lead detecting ventricle contraction and a second ventricle lead detecting ventricle contraction is greater than 30 milliseconds, and blocking Cardiac Contractility Modulation stimulation application.

According to some embodiments of the invention, the Cardiac Contractility Modulation stimulation application is blocked for just one cycle.

According to an aspect of some embodiments of the present invention there is provided a method of increasing peak VO2 including detecting ventricle contraction using one or more leads in a patient's ventricle, and applying Cardiac Contractility Modulation stimulation to the patient's ventricle, after a delay from a time of the detecting, thereby increasing the patient's peak VO2.

According to some embodiments of the invention, the applying Cardiac Contractility Modulation in the ventricle is performed during a ventricle refractory period and out of an atrial refractory period.

According to some embodiments of the invention, further including applying Cardiac Contractility Modulation to an atrium.

According to some embodiments of the invention, the detecting and the applying are repeated over a period of 12 weeks, and the increasing the patient's peak VO2 is seen after the 12 weeks.

According to an aspect of some embodiments of the present invention there is provided a method of increasing peak VO2 including detecting ventricle contraction using no more than two leads located in a patient's ventricle, and not using a lead located in the patient's atrium, and applying Cardiac Contractility Modulation stimulation to the patient's heart, after a delay from a time of the detecting, thereby increasing the patient's peak VO2.

According to some embodiments of the invention, the detecting includes detecting using just one lead located in the patient's ventricle, and the applying Cardiac Contractility Modulation stimulation to the patient's heart includes using the same one lead located in the patient's ventricle.

According to an aspect of some embodiments of the present invention there is provided a method of increasing peak VO2 including detecting ventricle contraction using no more than two leads located in a patient's ventricle, and not sensing using a lead located in the patient's atrium, and applying Cardiac Contractility Modulation stimulation to the patient's heart, even during atrial fibrillation (AF), thereby increasing the patient's peak VO2.

According to an aspect of some embodiments of the present invention there is provided a method of increasing peak VO2 including detecting ventricle contraction using one or more leads in a patient's ventricle, and applying Cardiac Contractility Modulation stimulation to the patient's ventricle, after a delay from a time of the detecting, thereby increasing the patient's NYHA class by at least one class relative to the patient's baseline.

According to an aspect of some embodiments of the present invention there is provided a method of increasing peak VO2 including detecting ventricle contraction using one or more leads in a patient's ventricle, and applying Cardiac Contractility Modulation stimulation to the patient's ventricle, after a delay from a time of the detecting, thereby increasing the patient's NYHA class by at least 0.5 class relative to the patient's baseline.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, some embodiments of the present invention may be embodied as a system, method or computer program product. Accordingly, some embodiments of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Some of the methods described herein are generally designed only for use by a computer, and may not be feasible or practical for performing purely manually, by a human expert. A human expert who wanted to manually perform similar tasks, such as providing an electric signal to a heart, might be expected to use completely different methods, e.g., making use of expert knowledge and/or the pattern recognition capabilities of the human brain, which would be vastly more efficient than manually going through the steps of the methods described herein.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

Figure 2A:
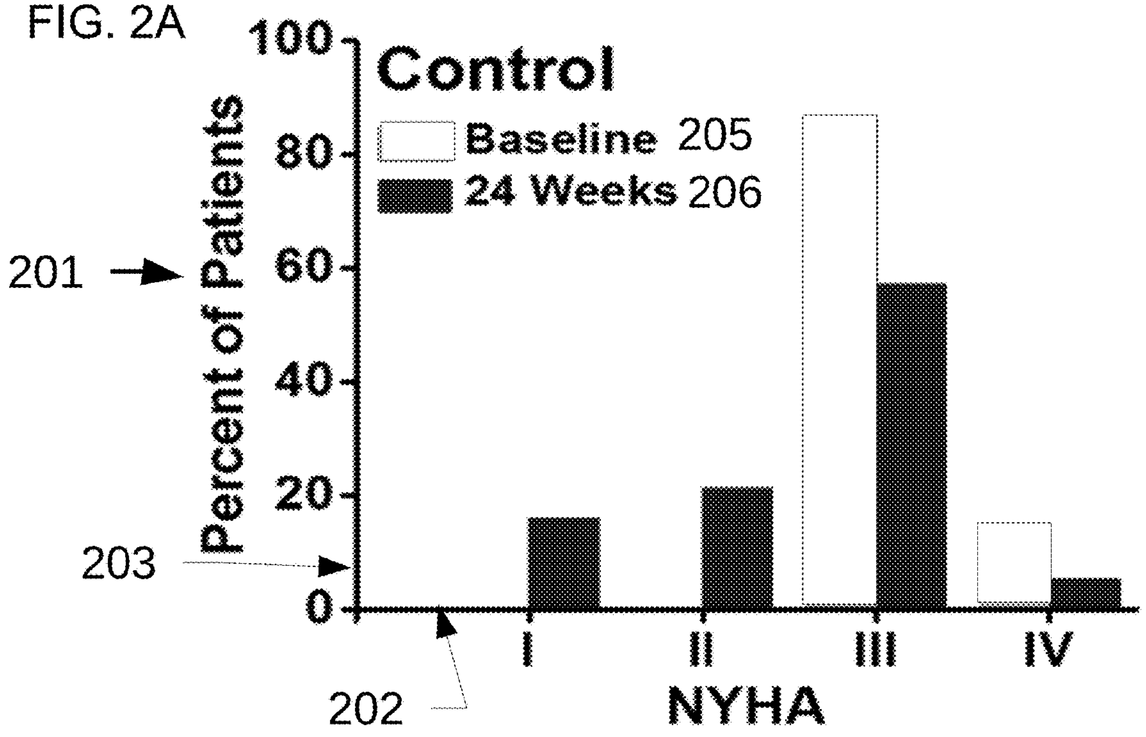
Figure 2B:
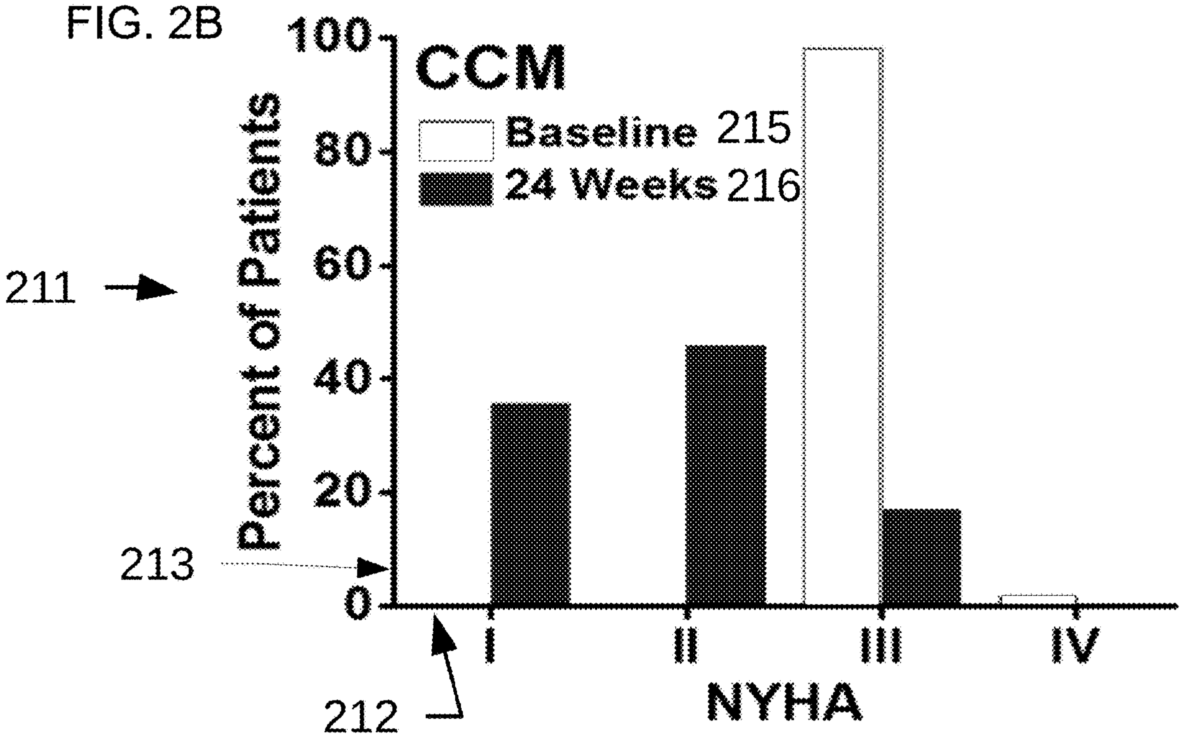
Figure 3A:
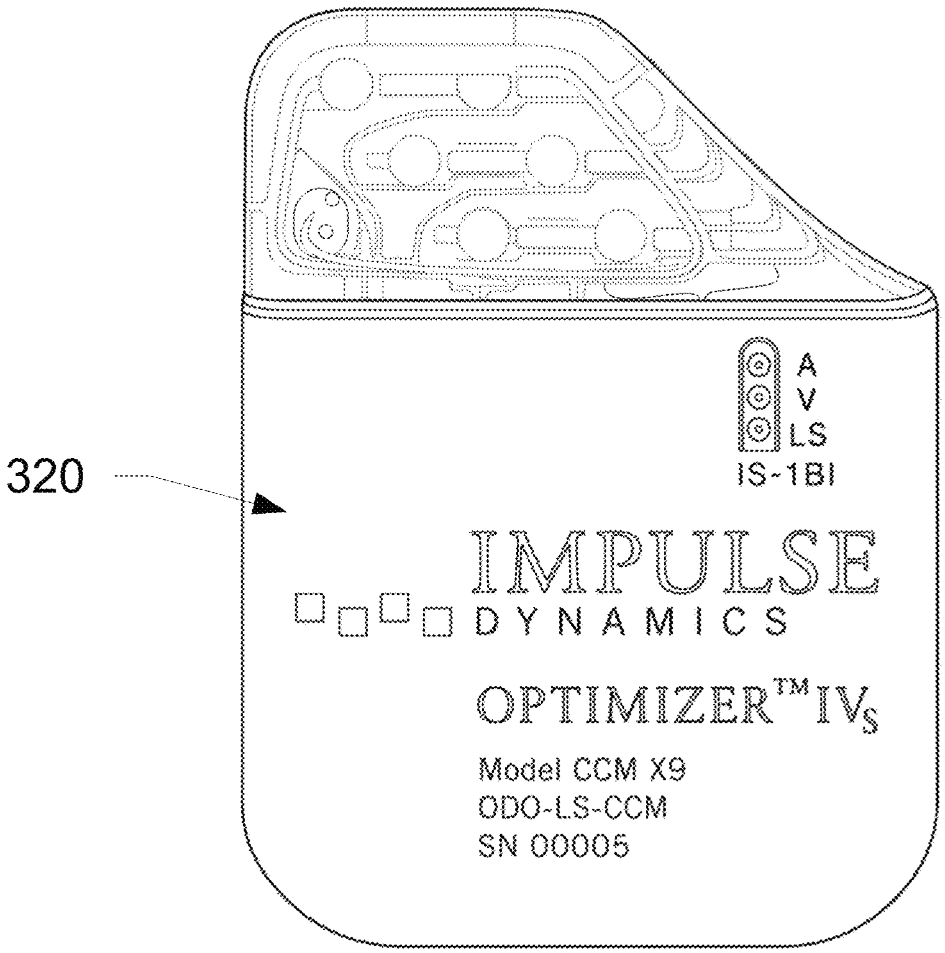
FIG. 3A PRIOR ART
Figure 3B:
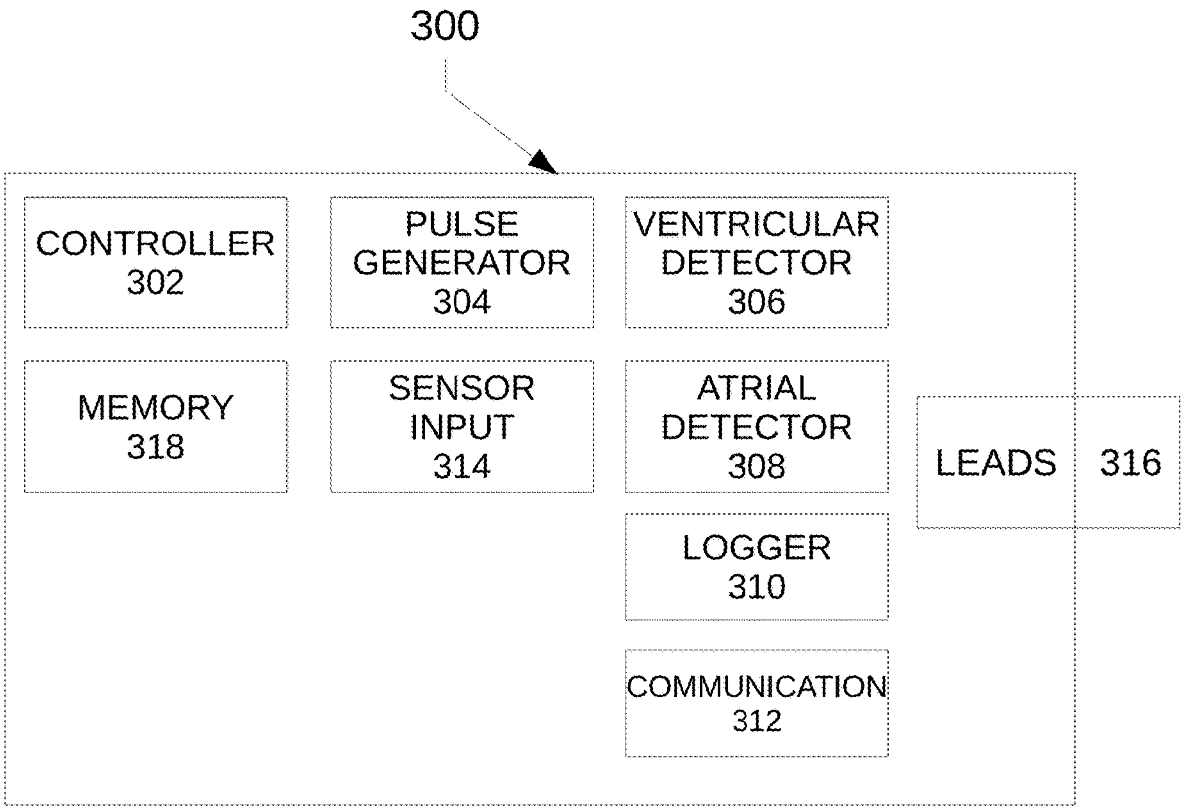
Figure 3C:
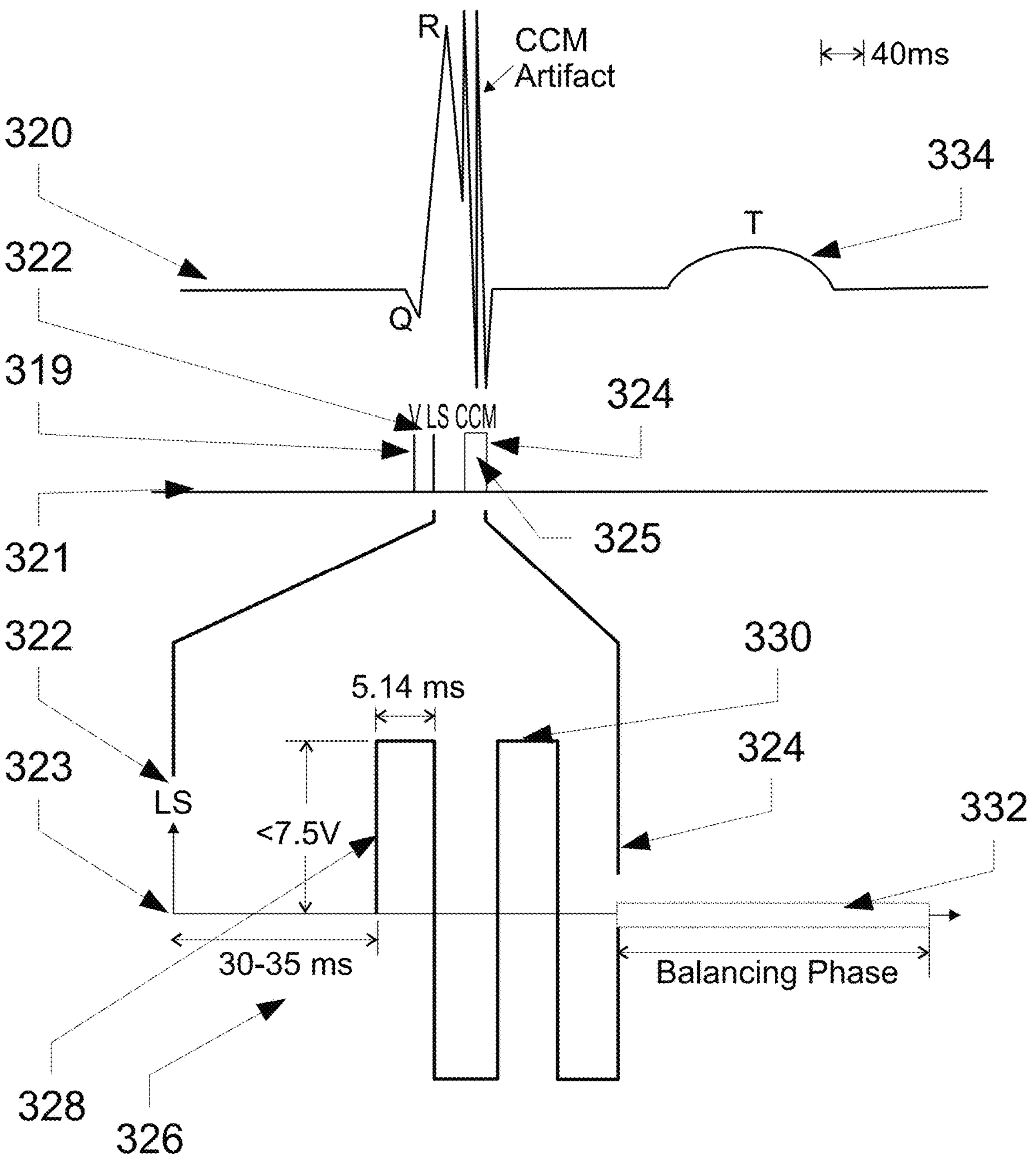
Figure 4:
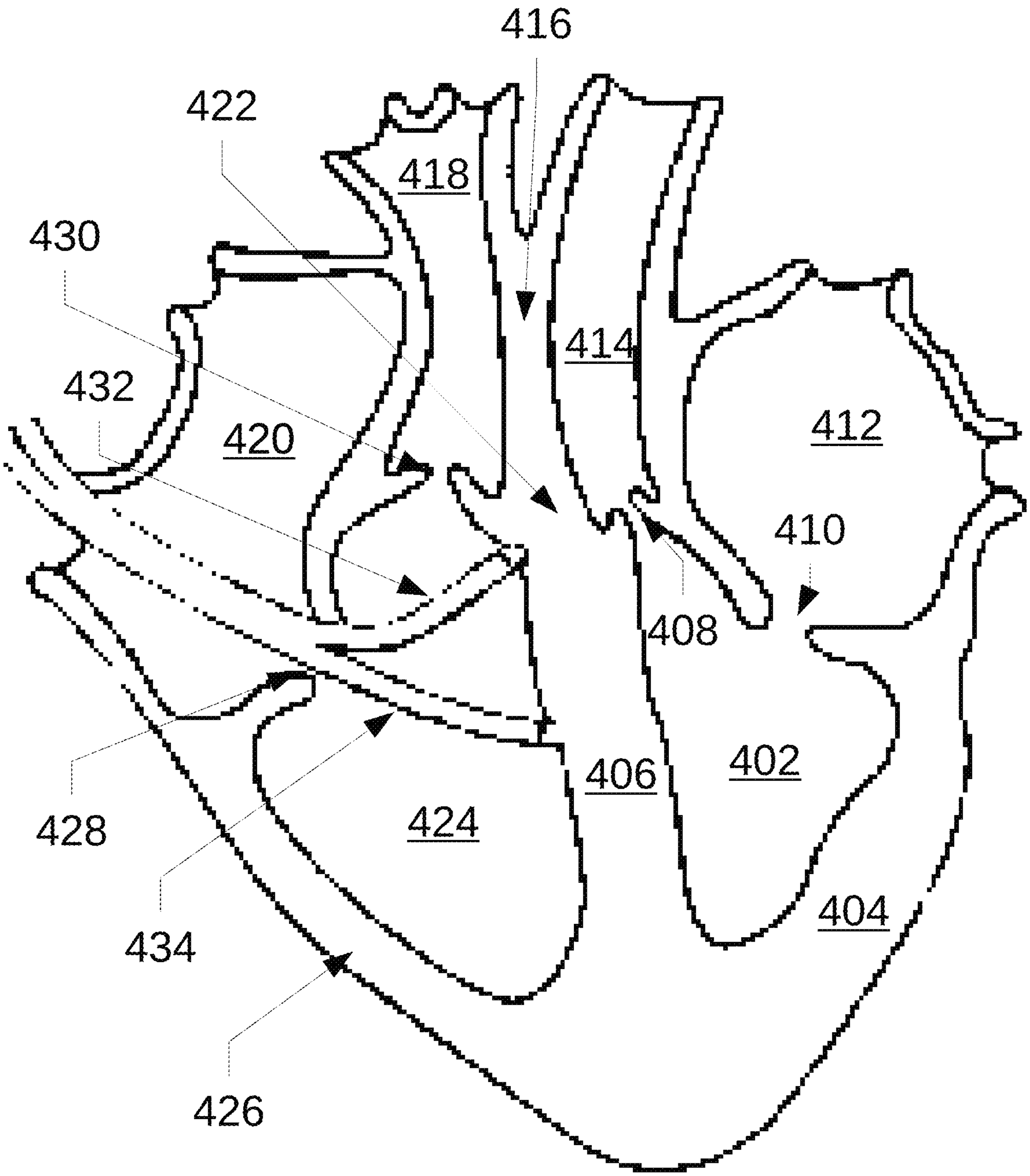
Figure 5A:
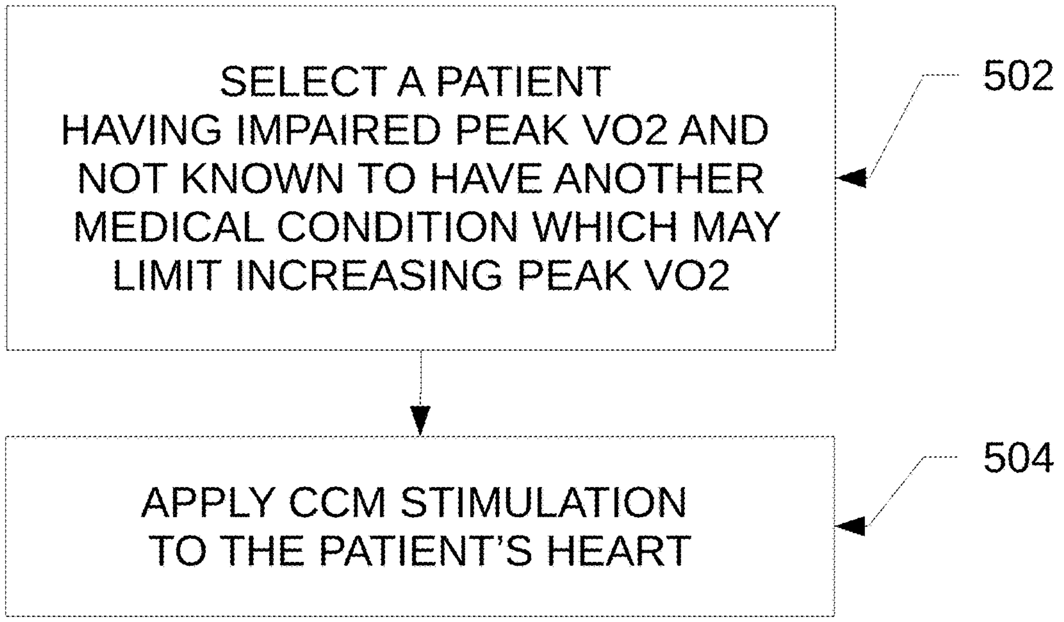
Figure 5B:
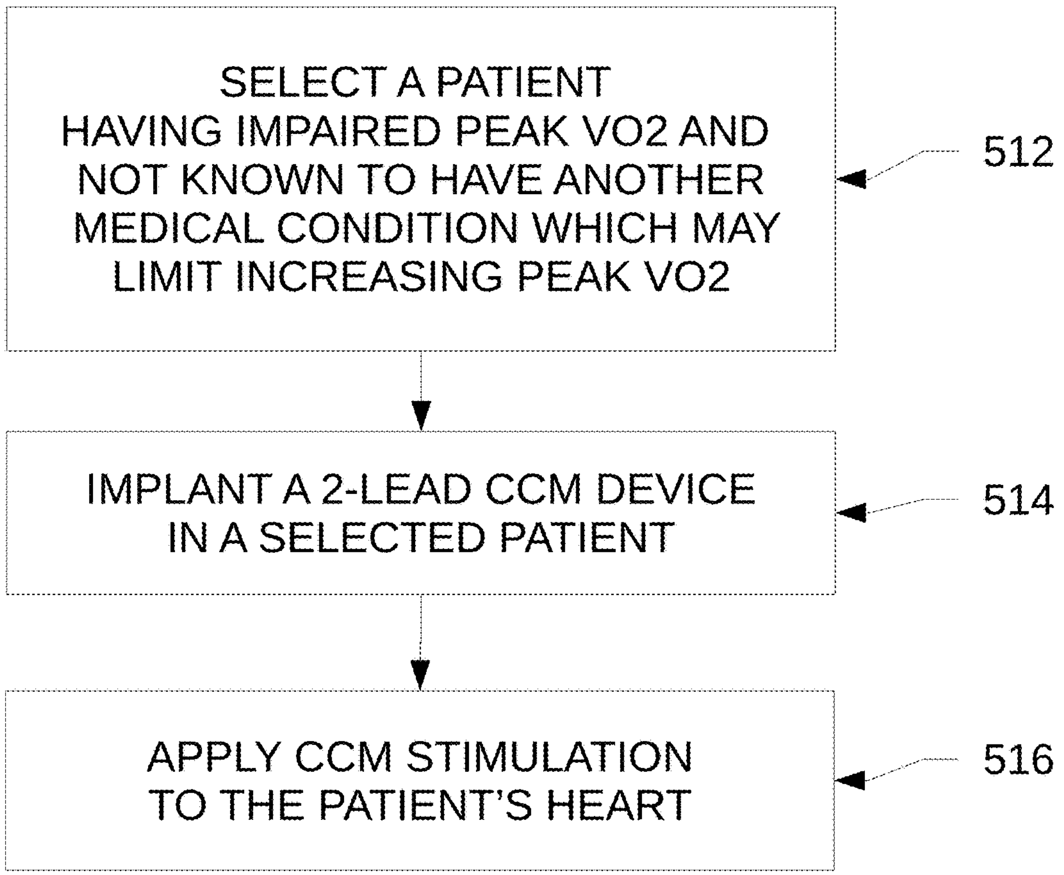
Figure 6:
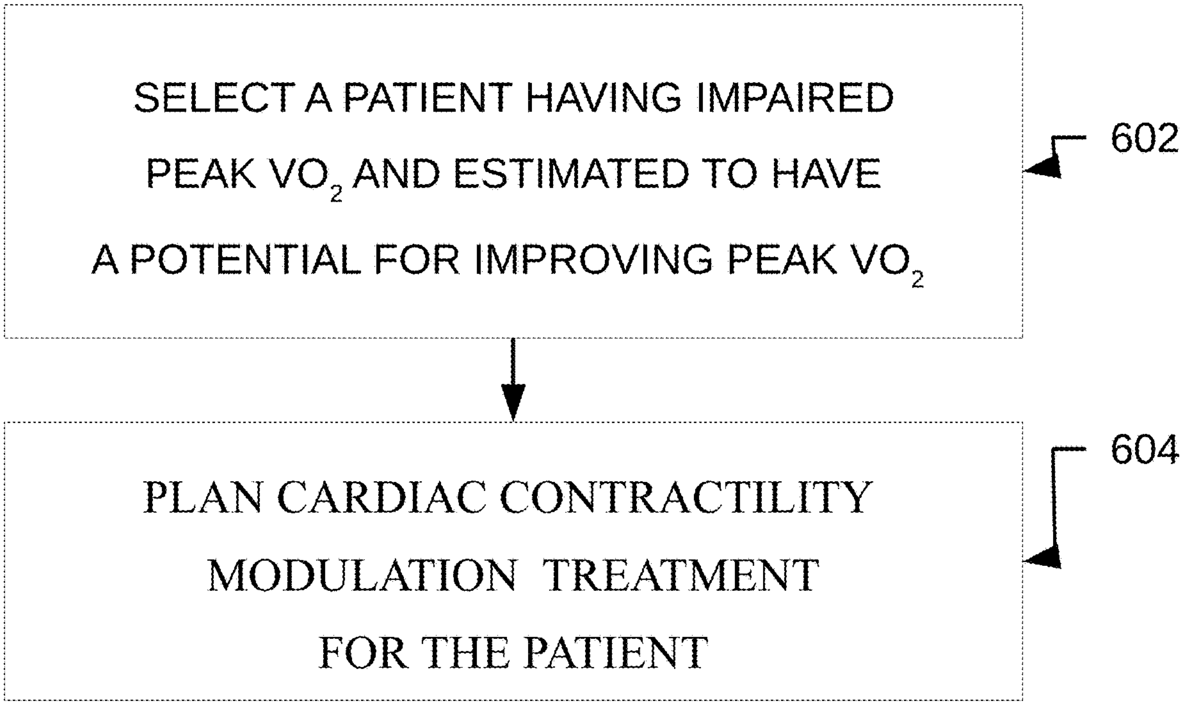

FIGS. 2A and 2B, which are graphs of New York Heart Association (NYHA) Functional Classification Distributions at baseline versus 24 weeks in the control group and in the 2-lead Optimizer group;

FIG. 3A is an image of a Cardiac Contractility Modulation device according to an example embodiment of the invention;

FIG. 3B is a simplified block diagram illustration of a cardiac therapy device according to an example embodiment of the invention;

FIG. 3C is a simplified line drawing of an ECG signal and a Cardiac Contractility Modulation stimulation signal according to an example embodiment of the invention;

FIG. 4 is a simplified line drawing illustration of a heart, showing various tissues and electrode/lead locations according to an example embodiment of the invention;

FIG. 5A is a simplified flow chart illustration of a method of increasing peak VO2 according to an example embodiment of the invention;

FIG. 5B is a simplified flow chart illustration of a method of increasing peak VO2 according to an example embodiment of the invention; and FIG. 6 is a simplified flow chart illustration of a method of planning Cardiac Contractility Modulation treatment for a patient to increase peak $VO_2$, according to an example embodiment.

DESCRIPTION OF SPECIFIC EMBODIMENTS OF THE INVENTION

The present invention, in some embodiments thereof, relates to using Cardiac Contractility modulation stimulation to increase peak $VO_2$ in patients.

Cardiac Contractility Modulation is a therapy which is intended for treatment of patients with heart failure with symptoms which can benefit from an improvement in cardiac output. The use of this therapy enhances the strength of ventricular contraction and therefore the heart's pumping capacity by modulating (adjusting) myocardial contractility.

Cardiac Contractility Modulation treatment is delivered by a pacemaker-like device that applies non-excitatory electrical signals (NES), adjusted to and synchronized with electrical action in the cardiac cycle. Other than a pacemaker, which delivers an electrical signal with an intention to result in cardiac contraction, the Cardiac Contractility Modulation treatment applies the NES, adjusted to and synchronized with the electrical action in the cardiac cycle.

In Cardiac Contractility Modulation therapy, electrical stimulation is applied to the cardiac muscle during the absolute refractory period. In this phase of the cardiac cycle, electrical signals cannot trigger new cardiac muscle contractions, hence this type of stimulation is known as a non-excitatory stimulation.

It is noted that in some embodiments the Cardiac Contractility Modulation signal may be excitatory to tissue other than that to which it is applied. Various mechanism by which Cardiac Contractility Modulation signals may operate are described, for example in "Cardiac contractility modulation: mechanisms of action in heart failure with reduced ejection fraction and beyond" by C. Tschope et al, European Journal of Heart Failure (2018), doi:10.1002/ejhf.1349 and may serve to guide in selecting signal application parameters in order to utilize and/or comply with one or more of these mechanisms.

For purposes of better understanding some embodiments of the present invention, as illustrated in FIGS. 1A, 1B, 2A, 2B, 3B, 4-5B and 6 of the drawings, reference is first made to the construction and operation of a Cardiac Contractility Modulation device as illustrated in FIG. 3A.

Reference is now made to FIG. 3A, which is an image of a Cardiac Contractility Modulation device according to an example embodiment of the invention.

FIG. 3A shows a Cardiac Contractility Modulation device 320 which can be used to provide Cardiac Contractility Modulation therapy to increase peak $VO_2$ in patients.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways.

Executive Summary

An aspect of some embodiments of the present invention relates to selecting patients with potential to increase their Peak $VO_2$ using Cardiac Contractility Modulation therapy; in some embodiments selecting based on their pulmonary reserve.

An aspect of some embodiments of the present invention relates to treating patients using Cardiac Contractility Modulation therapy to increase their peak VO2.

An aspect of some embodiments of the present invention relates to treating patients using Cardiac Contractility Modulation therapy without having an atrial lead and/or without using atria sensing and/or ignoring the atrial state; in some embodiments using just two ventricle leads; in some embodiments using just one ventricle lead, optionally using morphology to assess whether patient has ventricular arrhythmia. In some embodiments, applying Cardiac Contractility Modulation therapy without input from an atrial lead potentially ignores atrial fibrillation (AF), and potentially performs Cardiac Contractility Modulation stimulation even during AF. In such embodiments the Cardiac Contractility Modulation does (number of Cardiac Contractility Modulation stimulations per unit of time) potentially increases relative to sensing AF and not providing Cardiac Contractility Modulation stimulation when AF is detected.

Overview

An aspect of some embodiments of the present invention relates to selecting patients for which to plan cardiac contractility modulation treatment to increase Peak $VO_2$.

In some embodiments, if a patient has an implant capable of providing cardiac contractility modulation treatment in addition to whatever other treatment the implant can provide, plan to provide cardiac contractility modulation treatment based on the patient's cardiac condition and/or the patient's pulmonary condition.

In some embodiments, the patient's pulmonary condition is evaluated for suitability for providing cardiac contractility modulation to increase Peak $VO_2$. In some embodiments, the patient's pulmonary condition is evaluated for existence of pulmonary limitations as described further below. If the patient's pulmonary condition is such that the patient can benefit from an improvement in Peak $VO_2$, plan to provide cardiac contractility modulation treatment, either with additional cardiac treatment(s), or cardiac contractility modulation treatment on its own.

In some embodiments, the patient's cardiac condition is evaluated to determine whether a cardiac treatment in addition to cardiac contractility modulation should be provided. If the patient's cardiac condition is such that the patient can benefit from an improvement in Peak $VO_2$, then plan to provide cardiac contractility modulation treatment. If the patient's cardiac condition indicated that additional cardiac treatment is desirable, optionally plan providing cardiac contractility modulation treatment with additional cardiac treatment(s), by electric stimulation and/or medications.

In some embodiments, a treatment plan for the patient is selected, which may include providing only cardiac contractility modulation treatment; providing cardiac contractility modulation treatment in combination with treatment for the patient's cardiac condition; or not providing cardiac contractility modulation treatment.

In some embodiments, a potential patient is identified, test are performed to assess and/or quantify one or more of the patient's pulmonary and cardiac condition, and a cardiac contractility modulation treatment is optionally selected that is suitable, or even most suitable, for the patient.

An aspect of some embodiments of the invention relates to a planning process for patients. In some embodiments of the invention, a patient with impaired peak $VO_2$ or a risk of impaired peak $VO_2$ and who may have heart failure, is presented. Such a patient is optionally treated using cardiac contractility modulation treatment, for example, by implanting a therapeutic device and/or by reprogramming an already implanted device. Treatment of a patient using electrical stimulation may cause side effects and may also require tradeoff between different results, for example, pain level.

In some embodiments of the invention, an initial treatment is set and the treatment parameters are changed and/or an implanted device is reprogrammed, according to the effect of the treatment. It is noted such reprogramming may be needed even when an initial treatment plan appears optimal, for example, due to a change in the physiological state of the patient.

In some embodiments of the invention, a caregiver considers a plurality of considerations (e.g., as described herein), including, for example, a level of pain, a desired effect of increasing peak $VO_2$, a desired heart-failure related effect, potential effect of locations of electrodes and leads, and/or type of existing cardiac arrhythmia (e.g., ventricular) of the patient.

In some embodiments of the invention, a computer or table is used to decide on an initial therapy. For example, the computer may include rules or tables that indicate parameters and their expected effects and a caregiver may select or be offered a treatment plan that meets the various requirements set. Optionally or additionally, a caregiver can input such a proposed treatment plan and have it evaluated by such computer.

In some embodiments of the invention, the computer is programmed using a data set collating one or more therapeutic effects of one or more treatment plans with one or more parameters on patients with one or more characteristics. In some embodiments of the invention, such a data set is analyzed using machine learning methods to generate a parametric model (or other model) which can be queried to evaluate an expected range of effects of a treatment on a patient, or which can be used to automatically or semi-automatically search for proposed therapies.

An aspect of some embodiments of the present invention relates to selecting patients for application of Cardiac Contractility Modulation therapy to increase Peak V02.

Cardiac Contractility Modulation therapy is potentially increases of flow of oxygenated blood by between, for example, 5%-20%, 20%-40%, 40%-60%, 60%-100%, 100%-200% and/or intermediate or greater percentages relative to rest in a patient.

Cardiac Contractility Modulation therapy potentially improves peak VO2 in patients, over their baseline peak VO2, during Cardiac Contractility Modulation therapy.

Cardiac Contractility Modulation therapy potentially improves peak VO2 in patients, over their baseline peak VO2, even after Cardiac Contractility Modulation therapy has stopped. In some embodiments, patients selected include patients having CHF.

In some embodiments, patients are selected based on their NYHA Functional Classification. In some embodiments, patients are selected from NYHA classes II, III, IVa. Such patients can potentially benefit from Cardiac Contractility Modulation therapy, and potentially gain rise I their functional classification 1 full NYHA functional class, or at least a partial class, e.g. half a class, relative to their baseline, before Cardiac Contractility Modulation therapy.

In some embodiments of the invention, patients are selected for treatment based on an indication that peak $VO_2$ is limited by cardiac considerations.

In some embodiments, patients selected include patients having atrial fibrillation (AF), even permanent AF. In some embodiments, Cardiac Contractility Modulation therapy is provided by leads in the cardiac ventricle, and an atrial rhythm of a patient optionally does not influence providing the Cardiac Contractility Modulation therapy.

In some embodiments Cardiac Contractility Modulation therapy is optionally provided during a ventricle refractory period and out of the atrial refractory period, potentially enabling a longer delay after R wave detection relative to Cardiac Contractility Modulation therapy limited to be within the atrial refractory period.

In some embodiments, Cardiac Contractility Modulation therapy is optionally provided to the atria at any time. Such stimulation potentially does not affect cardiac HR, due to an atrial fibrillation condition.

In some embodiments, strong Cardiac Contractility Modulation stimulation is optionally provided, that can activate the ventricle during the ventricle refractory period.

In some embodiments, lower amplitude stimulation, that does not activate the ventricle, is optionally provided at any time.

In some embodiments, patients selected include patients such as participated in the study described below, falling into New York Heart Association (NYHA) Functional Classification II/III/IVa.

In some embodiments, patients selected include patients who are not known to have additional limitations, other than cardiac, for Cardiac Contractility Modulation to increase their peak VO2.

Such additional limitations may include:

- a limitation in pulmonary intake of oxygen, such as caused by lung disease;
- a limitation on blood flow, such as caused by blood vessel limitations;
- a limitation in peripheral blood flow, such as caused by peripheral blood vessel impairment;

In some embodiments patients selected for Cardiac Contractility Modulation therapy to increase Peak $VO_2$ are patients which do not have a pulmonary limitation, or do not have pulmonary limitation above a specific limit.

It is noted that increase in peak $VO_2$ may require a patient to have some pulmonary reserve. Optionally, patients are selected if their breathing reserve (e.g., potential increase in pulmonary effectiveness) is at least 10%, at least 20% at least 30%, at least 50% and/or intermediate or greater values. Breathing Reserve (BR) below 30% is often considered low and indicative of a pulmonary disorder which may be limiting on peak $VO_2$ improvement. BR may be defined as a difference between the maximal voluntary ventilation (MVV) and the maximum ventilation measured during an exercise test.

In some embodiments of the invention, patients are considered to potentially have a useful pulmonary reserve based on their oxygen uptake efficiency slope (OUES), for example, it being below 95%, 90%, 85%, 70% or intermediate values.

In some embodiments of the invention, patients are considered to potentially have a useful pulmonary reserve based on their peak RER, for example, being above, for example, 1, 1.05, 1.1, 1.15 or intermediate values.

In some embodiments of the invention, patients are considered to potentially have a useful pulmonary reserve based on their AT being low, rather than normal or crossed.

In some embodiments of the invention, patients are considered to potentially have a useful pulmonary reserve based on their VE/VCO2 ratio being above, for example, 25, 30, 35 or intermediate values.

In some embodiments of the invention, patients are considered to potentially have a useful pulmonary reserve based on their O2 saturation not falling and/or not falling rapidly during exercise, for example, falling less than 20%, 10%, 5% or intermediate values over a period of 20 minutes of exercise.

In some embodiments patients selected for Cardiac Contractility Modulation therapy to increase Peak $VO_2$ include patients with one or more of the following:

- Atrial Fibrillation (AF);
- Systolic heart failure (HF);
- Diastolic HF;
- Atrial Tachycardia;
- Angina;
- Myocarditis;
- Small vessel disease;
- Pulmonary hypertension;
- Chronic Obstructive Pulmonary Disease (COPD);
- Sleep Apnea;
- peak VO2 measured at less than, for example, 20 ml $O_2$/min/kg, or even 25 ml $O_2$/min/kg—patients that can potentially benefit from increasing peak VO2;
- peak VO2 measured at more than, for example, 9 ml $O_2$/min/kg, or even 5 ml $O_2$/min/kg.

In some embodiments patients at high risk are not selected for treatment by Cardiac Contractility Modulation therapy.

In some embodiments patients at high risk are also selected for treatment by Cardiac Contractility Modulation therapy.

In some embodiments of the invention, patients with a higher Peak VO2 are assumed to have more pulmonary reserve.

An aspect of some embodiments of the present invention relates to selecting a lead configuration to use in application of Cardiac Contractility Modulation therapy to increase Peak $VO_2$.

How Many Leads

In some embodiments, the number of leads for use in Cardiac Contractility Modulation therapy is selected.

In some embodiments, when a patient does not already have a Cardiac Contractility Modulation device and leads implanted, a Cardiac Contractility Modulation device with two leads is selected for implantation. It is noted that a potential benefit of a reduction of a number of leads, and specifically a reduction of an atrial lead, is having less leads in the veins. A potential benefit of a reduction of a number of leads includes reducing vessel blockage(s) and/or reducing superior vena cava syndrome.

In some embodiments, when a patient already has a Cardiac Contractility Modulation device and leads implanted, the Cardiac Contractility Modulation device is optionally programmed to sense the heart and/or apply Cardiac Contractility Modulation therapy using just two leads.

In some embodiments, the Cardiac Contractility Modulation device is optionally programmed to sense the heart and/or apply Cardiac Contractility Modulation stimulation using more than just two leads.

In some embodiments, the Cardiac Contractility Modulation device is optionally programmed to sense the heart with different leads than used for applying Cardiac Contractility Modulation stimulation.

In some embodiments, one or more of the leads are optionally used both for sensing and for applying Cardiac Contractility Modulation stimulation.

In some embodiments, one or more of the leads include one electrode or contact.

In some embodiments, one or more of the leads include a bipolar lead with two electrodes or contacts.

In some embodiments, two leads are selected to be used in applying the Cardiac Contractility Modulation therapy, each one of the two leads with two electrodes.

In some embodiments, four leads are selected to be used in applying the Cardiac Contractility Modulation therapy.

Where Sensing

In some embodiments, just one or two leads are used in sensing the heart to determine when to apply Cardiac Contractility Modulation therapy.

In some embodiments, a third, additional lead is used for sensing electrical signals in the heart, to detect an appropriate time for applying Cardiac Contractility Modulation therapy. In some embodiments, the third sensing lead is optionally located in the atrium, optionally in the right atrium.

In some embodiments, two leads are selected to be used in applying Cardiac Contractility Modulation therapy, and a third, additional lead is used for sensing.

Where to Apply Cardiac Contractility Modulation Stimulation

An aspect of some embodiments of the present invention relates to selecting a location or locations for placing leads to use in application of Cardiac Contractility Modulation therapy to increase Peak $VO_2$.

In some embodiments, just two leads are selected to be used in applying Cardiac Contractility Modulation stimulation. In some embodiments, two leads are used, with each lead acting as one pole of a bipolar stimulation.

In some embodiments, when two leads are used for Cardiac Contractility Modulation stimulation, the two leads are optionally placed in locations as follows:

Both leads at the inter-ventricular septum;

Both leads in the right ventricle, and in some embodiments one or both against the inter-ventricular septum;

Both leads in the left ventricle, and in some embodiments one or both against the inter-ventricular septum;

One lead in the left ventricle and one lead in the right ventricle, and in some embodiments one or both against the inter-ventricular septum;

One lead in the atrium and one lead in the ventricle;

At least one lead located between the ventricle and atria; and

U.S. Pat. No. 9,713,723 titled "Signal Delivery through the Right Ventricular Septum" describes performing Cardiac Contractility Modulation therapy with two leads placed against the ventricular septum. In some embodiments, the method taught in the above-mentioned patent is used to perform Cardiac Contractility Modulation therapy with two leads placed against the ventricular septum.

In some embodiments, leads for applying Cardiac Contractility Modulation stimulation are placed in a ventricle, more toward an apical side of a heart than toward an atrial side, for example more than halfway from the atrium toward the apex, along the ventricle wall.

In some embodiments, when two leads are used, one of the two leads may be used for sensing.

In some embodiments, three leads are selected to be used in applying the Cardiac Contractility Modulation therapy. In some embodiments, when a patient does not already have a Cardiac Contractility Modulation device and leads implanted, a Cardiac Contractility Modulation device with three leads is selected for implantation.

In some embodiments, when two leads plus a sensing lead are used, the leads are optionally placed in locations as follows:

Two activation leads at the ventricular septum, by way of a non-limiting example as shown in FIG. 4, and a sensing lead (not shown in FIG. 4) in one of the left atrium or the right atrium;

An aspect of some embodiments of the present invention relates to selecting a type of Cardiac Contractility Modulation device to implant for use in application of Cardiac Contractility Modulation therapy to increase Peak $VO_2$.

Apparently it is enough to use a 2-lead Cardiac Contractility Modulation device to perform Cardiac Contractility Modulation therapy to increase Peak $VO_2$. U.S. Pat. No. 6,480,737 titled "Field Delivery Safety System Using Detection of Atypical ECG" describes how Cardiac Contractility Modulation can be performed without a lead for atrial sensing. In some embodiments, the method taught in the above-mentioned patent is used to perform Cardiac Contractility Modulation therapy without using atrial sensing.

In some embodiments one or more of the leads used for applying Cardiac Contractility Modulation stimulation is optionally used for sensing.

In some embodiments, when a patient does not already have a Cardiac Contractility Modulation device implanted, a 2-lead Cardiac Contractility Modulation device is selected for implantation to perform Cardiac Contractility Modulation therapy to increase Peak $VO_2$. It is noted that a potential benefit of a reduction of a number of leads, and specifically a reduction of an atrial lead, is having less leads in the veins.

In some embodiments, sensing leads are placed in a ventricle, more toward an apical side of a heart than toward an atrial side, for example more than halfway from the atrium toward the apex, along the ventricle wall or the inter-ventricular septum. Such sensing potentially senses a state of the ventricle more than a state of the atrium.

Application of a Cardiac Contractility Modulation Stimulation Signal

In some embodiments of the invention, A Cardiac Contractility Modulation stimulation signal may be applied at a time which is not a refractory (or absolute refractory) period in the atria, while being an absolute refractory period in the ventricle.

In some embodiments of the invention, the amplitude of a signal applied to treat an ongoing AA episode is allowed to be greater (e.g., by between 10% and 500%, for example, between 10% and 60%, 60% and 150%, 150% and 300%, 300% and 500%, or greater or intermediate percentages) than a chronic application. This may be, for example, due to pain or other side effects being less critical to a patient if the patient is aware of the treatment increase being transient and/or being for treating an acute medical condition.

An aspect of some embodiments of the invention relates to shortening a prohibition period after suspected arrhythmia, when applying Cardiac Contractility Modulation. In one example, a suspected ventricular arrhythmic beat causes a prohibition window of only a single or optionally no beats. Potentially, this allows the next Cardiac Contractility Modulation to act on the tissue which is still recovering from an arrhythmic beat. Possibly, this reduces pro-arrhythmic tendencies of an arrhythmic beat and/or otherwise improve functioning and/or potential healing of tissue with heart failure or other dysfunction. In some embodiments of the invention, the length of prohibition window depends on the number of arrhythmic beats (and/or a time duration of a ventricular arrhythmic episode). In some embodiments of the invention, there is no window of prohibition of atrial arrhythmic beats, even if there is a window for ventricular arrhythmic beats. In some embodiments of the invention, Cardiac Contractility Modulation signals are applied even when the atria is excitatory.

In some embodiments of the invention, the prohibition window is shortened and/or Cardiac Contractility Modulation applied during atrial excitatory times even in a heart without atrial arrhythmia and/or when there is no active atrial arrhythmia.

In some embodiments of the invention, a relatively low threshold for heart rate is used, for example, between about 90 or about 100 and about 110 beats BPM. Potentially, this prevents wasting energy on high heart rates (as they have more beats in a same time window and an exemplary treatment is a daily period of 7 hours) and/or may direct more of the applied energy to lower heart rates where the body is at rest.

In other embodiments a higher heart rate threshold may be used, for example, 120, 130, 140—or intermediate heart rates.

It is noted that heart rates may be measured approximately and/or rather than a threshold, some type of fuzzy decision making or hysteresis may be used to decide on prohibition. For example, a signal may be prohibited with a probability that depends on the heart rate. In another example, once heart rate goes down, the threshold may be higher or lower than the threshold for stopping treatment as heart rate increases.

In some embodiments of the invention, there are different prohibit windows for different heart rates. For example, between about 80 and 110 no arrhythmic prohibition window is applied and/or between 100 and 130 there is a one beat length prohibition window and between 120 and 160 there is a two beat prohibition window.

An Example Cardiac Therapy Device

Reference is now made to FIG. 3B, which is a simplified block diagram illustration of a cardiac therapy device according to an example embodiment of the invention.

While existing devices such as the Optimizer 4 sold by Impulse Dynamics may be used, other device designs may be used as well.

FIG. 3B shows a cardiac therapy device 300, as shown, includes one or more leads 316 (optionally two leads), which are optionally couplable to the device 300 at one or more can connectors (not shown).

A pulse generator 304 is optionally used to generate the signal, for example, including a power circuitry, for example, including one or more storage capacitors.

In some embodiments of the invention, a ventricular detector 306 is optionally provided and used to detect atypical ventricular activation, which can be a contra-indication to signal application.

In some embodiments of the invention, an atrial detector 208 is optionally provided and used to detect atypical atrial activation, which may be used as an input to decision making by the device 300.

A sensor input 314 may receive data from one or more sensors, for example electrical sensors or other sensors, such as flow, pressure and/or acceleration sensors. Data from the sensors is optionally further processed (e.g., by a controller 302 and/or detectors 306, 308) and are optionally be used as an input to decision making processes in the device 300.

A controller 302 is optionally provided, and optionally executes one or more logics to decide, for example, a timing and/or other parameters of a signal and/or if a signal is to be applied.

A memory 318 is optionally provided, for example, to store logic, past effects, therapeutic plan, adverse events and/or pulse parameters.

A logger 310 is optionally provided to store activities of the device 300 and/or of the patient. Such a log and/or programming may use a communication module 312 (e.g., of a type known in the art) to send data from the device 300, for example, to a programmer (not shown) and/or to receive data, for example, programming, for example, pulse parameters.

In some embodiments of the invention, Cardiac Contractility Modulation timing is selected according to an expected effect of cardiac drugs on refractory period, for example, to ensure that stimulation is during a refractory period. It is noted that a there are some indications that a signal applied near the end of a refractory period may have the effect of preventing a next activation, which may have an anti-arrhythmic. Timing such activation may depended, for example, on drug dosage and/or expected effect. Optionally, such effects are programmed in controller 302 and/or in memory 318.

Reference is now made to FIG. 3C, which is a simplified line drawing of an ECG signal and a Cardiac Contractility Modulation stimulation signal according to an example embodiment of the invention.

FIG. 3C shows, in its upper portion, a typical ECG signal 320, including a T wave 334. Below the ECG signal, FIG. 3C shows a timeline 321 of Cardiac Contractility Modulation-related events, and below the timeline 321 FIG. 3C shows an enlarged portion of the timeline 321 showing a timeline 323 of the Cardiac Contractility Modulation stimulation signal.

The timeline 321 of the Cardiac Contractility Modulation-related events shows a first event 319 of a first lead detecting ventricle contraction, a second event 322 of a second lead detecting ventricle contraction, and a third event of Cardiac Contractility Modulation stimulation 325, ending at a fourth event 324 of the end of the Cardiac Contractility Modulation stimulation 325.

The timeline 323 of the Cardiac Contractility Modulation stimulation signal shows just a portion of the timeline 321 of Cardiac Contractility Modulation-related events, expanded relative to the timeline 321 of Cardiac Contractility Modulation-related events.

Referring to the timeline 323 of the Cardiac Contractility Modulation stimulation signal—the timeline 323 starts with the time 322 when the Cardiac Contractility Modulation device detects the ventricle contraction, and includes:

A pulse delay 326, followed by a series of one or more Cardiac Contractility Modulation stimulation pulses having a specific pulse amplitude 328 and pulse width 330, followed by a balancing phase 332.

In some embodiments, the balancing phase starts before the T wave 334.

In some embodiments, the balancing phase starts after a beginning of the T wave 334.

Some example values for values of Cardiac Contractility Modulation stimulation parameters include:

- pulse delay—more than 20 mS following detection of ventricle contraction.
- pulse amplitude—more than 10/20/50/100 V and Energy up to 0.01/0.1/0.5/1 J.
- pulse width—using a longer-than 20 mS pulse
- pulse shape—a biphasic alternating pulse shape, typically with more than one cycle, FIG. 3C shows a non-limiting example of two cycles.
- Tachycardia limit <110 BPM (significantly lower than 145 bpm). When tachycardia is detected, Cardiac Contractility Modulation stimulation is optionally not performed.
- 1 cycle inhibition in case of detecting an improper beat. When an improper beat is detected, for example when one or two sensing lead do not detect a ventricle contact after a specific time following a previous ventricle contraction, Cardiac Contractility Modulation stimulation is not applied, for a period lasting, for example, 1 heartbeat cycle.

In some embodiments, the Cardiac Contractility Modulation stimulation pulse shape is not necessarily a square wave, by way of some non-limiting examples the pulse shape may be sinusoidal or triangular.

In some embodiments, Cardiac Contractility Modulation stimulation is applied outside the atrial refractory period.

Some non-limiting example values for Cardiac Contractility Modulation stimulation include:

Pulse amplitude 7.5V;

two biphasic pulses, each phase being approximately 5.14 ms wide;

a balancing phase (all participating electrodes shorted together to discharge electrode/tissue interface capacitances) duration of approximately 40 ms.

an LS-to-Cardiac Contractility Modulation pulse delay (pulse delay 326) approximately 30 ms to 35 ms.

In some embodiments, the pulse amplitude is optionally reduced if there is sensation until there is no sensation, optionally down to a minimum of 4.5V.

In some embodiments, sensing ventricle contraction is performed via two leads.

If detected contractions delay between the 2 leads is greater than 30 mS, that is define as an improper beat.

In some embodiments, for every improper beat detected Cardiac Contractility Modulation stimulation is not provided during a current and a following ventricle contraction.

In some embodiments, following detection of an improper beat, detection of ventricle contractions continues using 2 leads. Once 2 proper beats, for example proper beats are defined as a delay less than 30 mS between the 2 leads, are detected, Cardiac Contractility Modulation stimulation is again provided to the second cardiac contraction.

In some embodiments, such as, for example, the study described in the "Description of a Study" section below, all sensing is done in the ventricle.

In some embodiments of the invention, the atrial absolute refractory period is assumed to be about 0.15 seconds, followed by a relative refractory period of about 0.03 seconds. In some embodiments of the invention, the ventricular absolute refractory period is assumed to be between 0.25 and 0.3 seconds, with an additional relative period of 0.05 seconds. It is noted that these times can change between hearts and also under different conditions, such as pharmaceutical intake, anatomic excitation level, heart rate, recent arrhythmia and/or exercise. In some embodiments of the invention, the Cardiac Contractility Modulation stimulator is pre-programmed with parameters that take such refractory periods into account. Optionally, different numbers are used (e.g. stored in memory 218) for different conditions (e.g., different heart rates).

Reference is now made to FIG. 4, which is a simplified line drawing illustration of a heart, showing various tissues and electrode/lead locations according to an example embodiment of the invention.

FIG. 4 shows a heart 402 and heart parts: the left atrium 403, the right atrium 406. The left ventricle 404, the right ventricle 405, and the ventricular septum 407, also termed the inter-ventricular septum 407.

Referring first to parts of the heart, the following are indicated: a left ventricle 402 with an LV free wall 404, a ventricular septum 406, also termed the inter-ventricular septum 406, an aortic valve 408, a mitral valve 410, a left atrium 412, an aorta 414, an atrial septum 416, a pulmonary artery 418, a right atrium 420, an AV node 422 at a bottom of the atrial septum 416, a right ventricle 124 with an RV free wall 426, a tricuspid valve 428 and a pulmonary valve 430.

Also shown are a first stimulation lead 432 contacting the ventricular septum 406 with an electrode a second stimulation lead 434, contacting ventricular septum 406 with an electrode at a second location thereon. In some embodiments, a single lead may be used, which includes two spaced apart stimulation electrodes. In some embodiments, a lead may include one or more sensing electrodes.

While contact electrodes are noted, other types of electrodes may be used as well, for example, screw-in electrodes, sutured electrodes and free floating electrodes.

In some embodiments of the invention, the stimulation is bipolar, with one or more electrodes being bipolar electrodes (e.g., a pair), for example in the form of a tip surface and a ring electrode surface and/or acting themselves as a bipolar pair (e.g., one on each lead). Optionally or additionally, a remote electrode (e.g., a device can) acts as a second electrode, e.g., for unipolar stimulation.

The leads 432 and/or 434 may be dual use, for example, providing a pacing, cardioversion and/or defibrillation signal, in addition to a non-excitatory signal such as a Cardiac Contractility Modulation signal.

In some embodiments, the leads 432 and/or 434 may be used for sensing of electrical activity, optionally using the same electrodes as used for stimulation. In some embodiments, only one lead and/or only one electrode may be used for treatment. For example, a single ventricular or atrial lead may be used. Optionally or additionally, a lead outside of the chambers is used in addition to or instead of an intra-chamber lead, for example, in a coronary sinus or other blood vessel, outside the heart (e.g., on/attached to an external surface thereof and/or in a left side of the heart, for example, left ventricle 402 and/or left atrium 412).

It is noted that FIG. 4 is schematic and flattened. For example, in a real heart the left atrium 412 and the right atrium 420 both abut the atrial septum 416.

Reference is now made to FIG. 5A, which is a simplified flow chart illustration of a method of increasing peak VO2.

The method of FIG. 5A includes:

selecting a patient having impaired peak VO2 and not known to have another medical condition which may limit increasing peak VO2 (502); and applying cardiac contractility modulation stimulation to the patient's heart (504).

Reference is now made to FIG. 5B, which is a simplified flow chart illustration of a method of increasing peak VO2.

The method of FIG. 5B includes:

selecting a patient having impaired peak VO2 and not known to have another medical condition which may limit increasing peak VO2 (512);

implanting a 2-lead Cardiac Contractility Modulation device in a selected patient (514); and applying cardiac contractility modulation stimulation to the patient's heart (516).

In some embodiments, patients selected for Cardiac Contractility Modulation therapy in order to increase Peak $VO_2$ include patients having one or more of:

Atrial Fibrillation (AF);

Systolic heart failure (HF);

Diastolic HF;

Atrial Tachycardia;

Angina;

Myocarditis;

Small vessel disease;

Pulmonary hypertension;

Chronic Obstructive Pulmonary Disease (COPD); and

Sleep Apnea;

In some embodiments, patients selected for Cardiac Contractility Modulation therapy in order to increase Peak $VO_2$ include patients having:

peak VO2 measured at less than, for example, 20 ml $O_2$/min/kg, or even 25 ml $O_2$/min/kg—patients that can potentially benefit from increasing peak VO2;

peak VO2 measured at more than, for example, 9 ml $O_2$/min/kg, or even 5 ml $O_2$/min/kg—potentially not treating patients at high risk;

having peak VO2 between 9-25 $O_2$/min/kg are selected for treatment.

For example, in the study described in the "Description of a Study" section below, patients having peak VO2 between 9-25 $O_2$/min/kg were selected for treatment.

In some embodiments, patients selected for Cardiac Contractility Modulation therapy in order to increase Peak $VO_2$ include patients having one or more of:

A breathing reserve of over 20% or more (up to 50%). Breathing Reserve (BR) is usually determined during a pulmonary exercise stress test. It is the difference between the maximal voluntary ventilation (MVV) and the maximum ventilation measured during the exercise test. Some experts do not believe direct MVV measurement to be reliable because it is very effort dependent and is very difficult to put acceptability criteria together. However, FEV1 is well defined, when and how is it acceptable. Therefore, it is a fairly well-defined measure that can be used to predict the MVV. The formula for MVV, when derived from FEV1 is 40*FEV1 or some are using 35*FEV1.

$$BR(L/min)=MVV-Max\ VE. \quad \text{Calculation:}$$

$$BR\ \%=(MVV-VE/MVV)\times 100.$$

Example: If MVV=82 L/min and VE at max exercise is 65 L/min, Then: BR=82−65=17, BR %=(82−65/82)×100=21%

FEV1 is a measure of a person's vital capacity, that the person is able to expire in the first second of forced expiration;

Oxygen uptake efficiency slope (OUES)<89%;

Peak RER>1.1 The respiratory exchange ratio (RER) indirectly shows the muscle's oxidative capacity to get energy; and A constant peak Vo2 saturation for HF patients.

In the Study described in the "Description of a Study" section below, the following Cardiac Contractility Modulation signal was used: a series of two biphasic pulses, having a duration of 5.14 ms (milliseconds) per pulse phase, a voltage of 4.5V-7.5V and at a delay of between 30-35 ms after local activation at application location (using a bipolar lead) and followed by a charge balancing phase of 40 ms. It is noted that local activation is often shortly after start of ventricular activation. In the balancing pulse, all activated electrodes are shorted together. The voltage is probably reduced until there is a lack of sensation.

This signal can be modified. In some embodiments of the invention, the balancing phase can be omitted or provided with a different length, for example, between 1 and 200 ms, for example, between 10 and 50 ms, for example between 20 and 41 ms, or intermediate lengths. The top voltage can be increased from 7.5V, for example, to 8V, 9V, 10V, 12V, 20V, 40V, 100V or intermediate or small values. It is noted that as an acute effect, sensation may not be considered an issue.

The delay can be shorter, for example, between 1 ms and 30 ms, between 5 and 20 ms, between 10 and 25 ms or intermediate delays. The delay can be longer, for example, between 35 and 50 ms, 50 and 70 ms, or intermediate or smaller or greater delays. It is noted that longer delays may be acceptable in AA patients as causing an arrhythmia in atria (due to Cardiac Contractility Modulation being applied outside of atrial absolute refractory period), may not be an issue in patients with atrial fibrillation. It is noted that this may allow patients with long Av delays to be usefully treated (e.g., by ignoring atrial effects).

The number of phases may be modified as well, for example, being as few as 1, 2 or 3 or as many as 5, 10, 20, 50 or intermediate or greater numbers. The length of a phase may be modified, for example, being between 1 and 100 ms, for example, 2, 3, 5, 6, 6.6, 10, 15, 25, 50 ms or intermediate in length. Also, not all phases need to be the same length and/or same voltage. In addition, while square pluses are optionally used, other pulse shapes may be provided, for example, sinus, curved, triangular and/or symmetric or asymmetric. In some embodiments, there is an inter-phase delay, for example, 1, 2, 4, 5, 6 10, 20 ms or intermediate or smaller or greater delays.

The energy delivered in a beat may be, for example, 0.01, 0.1, 0.5, 1 J, 5 J, 10 J or intermediate or smaller or greater energy levels.

The duration during which pulses are applied to the heart in a beat can be, for example, 5 ms, 10 ms, 20 ms, 30 ms, 40 ms or intermediate or greater durations.

In some embodiments of the invention, any of the above numbers is varied by, for example, 5%, 10%, 20% or intermediate values.

It is noted that the delay may be a calculated delay (e.g., if patient is paced) or an approximation, for example, if two leads are used as a bipolar electrode, the lowest or an average activation time are optionally used to calculate the delay.

In some embodiments of the invention, the Cardiac Contractility Modulation treatment is applied for, for example, 1, 2, 3, 4, 5, 6, 7, 8, 10, 15, 24 or intermediate numbers of hours a day, for example, for 1, 2, 3, 4, 5, 8, 12, 24 weeks or intermediate or greater number of weeks. During a treatment time, each beat is optionally treated or intended to be treated. In other schemes, the treatment may be set according to a target of number of beats treated per day, for example, as noted herein.

It is noted that a Cardiac Contractility Modulation signal is sometimes not applied at a heart beat for reasons other than dosing. For example, the heart beat may be deemed unsafe in the sense that a Cardiac Contractility Modulation signal might cause an arrhythmia if applied during that beat. Optionally or additionally, the heart may be allowed to "recover" from an arrhythmic beat for one or more "prohibition" beats.

In some embodiments, eliminating use of an atrial lead was made through modifying an algorithm used to decide if to apply a Cardiac Contractility Modulation signal during a given beat to eliminate atrio-ventricular timing criteria, in some embodiments also at the same time strengthening criteria used to evaluate the timing and sequence between two ventricle leads.

In some embodiments of the invention (e.g., in the below described Study), the following algorithm is used to decide if to apply a Cardiac Contractility Modulation signal during a given beat:

A first optional section of the algorithm is avoiding stimulation with Cardiac Contractility Modulation is the heart rate is too high, for example, above a cutoff threshold, for example, 90, 100, 110, 120, 130, 140, 145, 160 or intermediate values. Optionally, this may prevent applying Cardiac Contractility Modulation during VT or incipit VT and/or other arrhythmia which may be detected as a high heart rate.

A second optional section of the algorithm is avoiding stimulation if a delay between two ventricular leads is above a certain threshold, for example, 30 ms, though other numbers may be used, for example, 10 ms, 20 ms, 40 ms, 50 ms and/or intermediate or greater thresholds. This delay may indicate multiple foci and/or irregular propagation direction in the ventricle.

An example specific algorithm comprises:

Sensing ventricle contraction in both ventricle leads determine that heart rate is below 110 BPM If detected contractions delay between the 2 leads is greater than 30 mS, define as improper beat For every detected improper beat do not provide Cardiac Contractility Modulation stimulation during the current and the following ventricle contraction (though in some embodiments, Cardiac Contractility Modulation may be provided on next beat and in others the delay may be more than one beat).

Following detection of improper beat, continue detection of ventricle contractions in 2 leads. Once 2 proper beats (delay less then 30 mS) are detected, deliver Cardiac Contractility Modulation stimulation in that cardiac contraction, at the preset delay.

In some embodiments of the invention, irregular beats are detected based on an AV delay and/or based on a morphology of an electrogram signal detected at one or more of the electrodes. Other methods of detecting potentially unsafe beats (e.g., beats where the ventricle may be stimulated outside of its absolute refractory period) may be used as well.

Reference is now made to FIG. 6, which is a simplified flow chart illustration of a method of planning Cardiac Contractility Modulation treatment for a patient to increase peak $VO_2$, according to an example embodiment.

The method shown in FIG. 6 includes:

selecting a patient having impaired peak VO2 and estimated to have a potential for improving peak VO2 (602); and planning Cardiac Contractility Modulation Treatment for the patient (604).

In some embodiments, the selecting includes selecting a patient who already has an implant suitable for providing Cardiac Contractility Modulation treatment.

In some embodiments, the selecting includes selecting a patient not known to have another medical condition which may prevent increasing peak VO2.

In some embodiments, the selecting includes selecting a patient estimated to have a pulmonary reserve.

In some embodiments, the patient's pulmonary condition is evaluated for suitability for providing cardiac contractility modulation to increase Peak $VO_2$ as described below. In some embodiments, the patient's pulmonary condition is evaluated for existence of pulmonary limitations as described further below. If the patient's pulmonary condition is such that the patient can benefit from an improvement in Peak $VO_2$, plan to provide cardiac contractility modulation treatment, either with additional cardiac treatment(s), or cardiac contractility modulation treatment on its own.

In some embodiments, the patient's cardiac condition is evaluated to determine whether a cardiac treatment in addition to cardiac contractility modulation should be provided. If the patient's cardiac condition is such that the patient can benefit from an improvement in Peak $VO_2$, then plan to provide cardiac contractility modulation treatment. If the patient's cardiac condition indicated that additional cardiac treatment is desirable, optionally plan providing cardiac contractility modulation treatment with additional cardiac treatment(s).

In some embodiments, a treatment plan for the patient is selected, which may include providing only cardiac contractility modulation treatment; providing cardiac contractility modulation treatment in combination with treatment for the patient's cardiac condition; or not providing cardiac contractility modulation treatment.

Description of a Study

Reference is now made to the following description of a Study, which together with the above descriptions illustrate some embodiments of the invention in a non-limiting fashion.

The following example describes Safety, Performance and Efficacy of Cardiac Contractility Modulation Delivered by a 2-lead Optimizer Smart System, named "The FIX-HF-5C2 Study".

Introduction: One purpose of this study was to test the performance, safety and clinical effects of a 2-lead system compared to a 3-lead system.

Methods: Patients could participate if they had NYHA III/IVa symptoms despite appropriate medical therapy, LVEF 25-45% and were not eligible for CRT. All subjects received an Optimizer 2-lead implant and were seen at 12- and 24-weeks. Device interrogation provided a number of Cardiac Contractility Modulation signals effectively delivered. A primary endpoint was an estimated difference in a change of peak $VO_2$ from baseline to 24 weeks between FIX-HF-5C2 (2-lead device) subjects relative to control subjects from a prior FIX-HF-5C study. A primary safety endpoint was an assessment of a rate of device-related adverse events between FIX-HF-5C2 (2-lead device) subjects compared to FIX-HF-5C (3-lead device) subjects.

Results: 60 subjects, 88% male, age 66±9 years, with LVEF 34±6%, 68% having ischemic cardiomyopathy, and 15% with atrial fibrillation were included. Cardiac Contractility Modulation delivery did not differ between 2- and 3-lead systems (19,892±3472 vs 19,583±4998 pulses/day). A change of peak VO2 from baseline to 24 weeks was 1.72 (95% Bayesian credible interval [BCI]:1.02, 2.42) ml/kg/min greater in the 2-lead device group versus the control group. Adverse events did not differ between groups except for a decrease in Optimizer-related adverse events (0% vs 8%, p=0.03) in the 2-lead group compared to the 3-lead group.

Some Conclusions: The 2-lead system effectively delivers a comparable amount of Cardiac Contractility Modulation pulses (including in subjects with atrial fibrillation) as the 3-lead system, is equally safe and improves peak VO2 and NYHA functional class. Device-related adverse effects are less with the 2-lead system.

Cardiac contractility modulation is an electrical device-based therapy developed for treatment of chronic heart failure. Cardiac Contractility Modulation signals are non-excitatory electrical signals applied during a cardiac absolute refractory period that typically favorably impact the biology of the failing myocardium.

Cardiac Contractility Modulation has been studied in several randomized studies, including a double blind, double crossover study in Europe (the FIX-HF-4 study), a blinded randomized pilot study in the US, a prospective randomized study in the US including 428 subjects (the FIX-HF-5 trial), and a second prospective randomized study in the US and EU that included 160 subjects (the FIX-HF-5C study). Collectively, the results of these prior randomized studies indicated that Cardiac Contractility Modulation improves functional class, quality of life and exercise tolerance, particularly in patients with LV EFs (Left Ventricle Ejection Fractions) between 25% and 45%, NYHA III symptoms despite guideline-directed medical therapy (and an ICD if indicated), normal QRS duration (i.e., not indicated for CRT) and sinus rhythm. Based on these findings, the Optimizer system received approval for use in this patient population by the US Food and Drug Administration. Additional information from registry studies have suggested that LV EF is improved by approximately 5 percentage points, that clinical effects are sustained through 2 years of follow up, and Cardiac Contractility Modulation therapy is associated with reduced rates of heart failure hospitalizations compared to the number of hospitalizations observed the year prior to Optimizer system implant.

All of the aforementioned studies were performed with an Optimizer device that employs 3 leads placed in the heart: one to the right atrium and two to the right ventricular septum. While the RV septal leads are used for both sensing and Cardiac Contractility Modulation signal delivery, the atrial lead is used only for sensing the timing of atrial depolarization. That information was used as input to an algorithm that ensured proper timing of Cardiac Contractility Modulation signal delivery during the myocardial absolute refractory period, including suppression of Cardiac Contractility Modulation delivery on premature ventricular contractions. This requirement imposed a technical limitation for the use of Cardiac Contractility Modulation in patients with atrial fibrillation or flutter. The Cardiac Contractility Modulation signals delivered by the 2- and 3-lead Optimizer systems were identical, however, the upper atrial rate above which Cardiac Contractility Modulation signal delivery was inhibited could be set as high as 179 bpm in the 3-lead system, whereas this upper limit with the 2-lead system is 110 bpm. In addition, as with cardiac rhythm devices in general, device-related adverse events have mainly been related to the leads (see for example) so that reduction of the number of leads has a potential to reduce adverse events.

A new Cardiac Contractility Modulation delivery algorithm has been developed that eliminates the need for an atrial sensing lead, which has led to the development of a 2-lead Optimizer device. The FIX-HF-5C2 study was a prospective, multicenter, single-arm study designed to test the performance, safety and clinical effects of this 2-lead Optimizer Smart System.

Methods

Sixty subjects were enrolled from 7 medical centers in the United States and 1 medical center in Germany. Subjects were evaluated at baseline and again at 12- and 24-weeks after implant. The inclusion and exclusion criteria are summarized in Table 1. Major criteria included: adult subjects with LV EF≥25% and ≤45% by echocardiography (assessed by core laboratory); NYHA III or ambulatory IV symptoms despite 90 days of guideline-directed heart failure medical therapy (including ICD when indicated) that was stable for 30 days prior to enrollment; and, not indicated for cardiac resynchronization therapy (CRT). Patients were excluded if they were hospitalized for heart failure requiring intravenous loop diuretics, inotropes or hemofiltration within 30 days; if they were receiving any form of positive inotropic support within 30 days before enrollment; if peak VO2 on cardiopulmonary stress testing (CPX) was <9 or >20 ml $O_2$/min/kg (assessed by core laboratory); if they had a potentially correctible cause of heart failure (e.g., valvular or congenital heart disease); if exercise tolerance was limited by a condition other than heart failure; or if they were schedule for or had recent CABG, PCI or MI. Notably, in comparison to all prior studies in the United states, patients with atrial fibrillation could be enrolled.

TABLE 1

| Inclusion and exclusion criteria. |
|---|
| Inclusion Criteria: |
| 1. 18 years of age or older |
| 2. Male or a nonpregnant female |
| 3. Baseline ejection fraction ≥25% and ≤45% by echocardiography core laboratory. |
| 4. NYHA III or IV despite guideline-directed medical therapy for heart failure for at least 90 days (including treatment with a β-blocker for at least 90 days unless intolerant) |
| a. medical therapy is stable defined as no more than a 100% increase or 50% decrease in dose during the 30 days prior to enrollment |
| b. ICD if indicated |
| 5. Willing and able to return for all follow-up visits. |
| Exclusion Criteria: |
| 1. Peak $VO_2$ <9 or >20 ml $O_2$/min/kg. The qualifying CPX test must be deemed adequate. |
| 2. Subjects who have a potentially correctible cause of heart failure (e.g., valvular or congenital heart disease) |
| 3. Clinically significant angina pectoris, an episode of unstable angina within 30 days, or angina and/or ECG changes during exercise testing performed during baseline evaluation. |
| 4. Hospitalized for heart failure requiring acute treatment with intravenous loop diuretics, IV inotropes or hemofiltration within 30 days, or receiving any form of positive inotropic support within 30 days before enrollment, including continuous IV inotrope therapy. |
| 5. PR interval greater than 375 ms. |
| 6. Exercise tolerance is limited by a condition other than heart failure or unable to perform baseline stress testing. |
| 7. Scheduled for CABG or PCI, or has undergone a CABG within 90 days or PCI within 30 days. |
| 8. Biventricular pacing system, an accepted indication for such a device, or a QRS width of 130 ms or greater. |
| 9. Myocardial infarction within 90 days. |
| 10. Mechanical tricuspid valve |
| 11. Prior heart transplant. |
| 12. Chronic hemodialysis. |
| 13. Participating in another experimental protocol. |
| 14. Unable to provide informed consent. |

The schedule of events is summarized in Table 2. Following eligibility determination, subjects underwent implantation of a 2-lead Optimizer Smart System. After device programming, subjects were generally discharged from the hospital the same day or the day following implantation. Subjects returned for routine wound and device checks (when Cardiac Contractility Modulation signal parameters were checked and optimized) after ~2 weeks. Study follow up visits for clinical assessments were conducted at 12- and 24-weeks (±2 weeks) following device implantation. In addition to an interim safety assessment, NYHA was determined by a site clinician and CPX tests were repeated at these visits.

The primary safety endpoint was the percentage of subjects experiencing an Optimizer device- or procedure-related complication through the 24-week follow up period. Complications were adjudicated by an independent events adjudication committee (EAC). The EAC reviewed, adjudicated, classified and validated all reported SAEs that occurred over the 24-week course of study. The classifications included whether the event was related to either the device or to the implant procedure, and whether such an event constituted a "complication" as defined by the EAC charter. The committee also adjudicated the cardiac and heart failure relatedness of deaths and hospitalizations.

TABLE 2

Study schedule of events

| Tests and Assessments | Screening/ Baseline | Optimizer Implant | Week 2 ± 7 days | 12 ± 2 Weeks | 24 ± 2 Weeks | 1 Year ± 1 mo | Every 6 months** |
|---|---|---|---|---|---|---|---|
| Informed Consent | X | | | | | | |
| Interim History | X | | X | X | X | X | X |
| NYHA Class (site clinician assessment) | X | | | X | X | | |
| Medications | X | | | X | X | | |
| Physical Examination | X | | | X | X | | |
| 12-Lead EKG* | X | | | | | | |
| NT-proBNP | X | | | X | X | | |
| Echocardiogram* | X | | | | | | |
| Cardiopulmonary Stress Test | X | | | X | X | | |
| Pregnancy Test | X | | | | | | |
| Eligibility determination | X | | | | | | |
| OPTIMIZER Smart System Implant | | X | | | | | |
| Chest X-ray (prior to hospital discharge) | | X | | | | | |
| OPTIMIZER Device Interrogation | | X | X | X | X | X | X |
| Safety Reporting | | X | X | X | X | X | X |

*12-Lead EKG and Echocardiogram test results (from the study-qualified lab) obtained within 30 days before informed consent and performed in accordance with the protocol, testing, and data collection requirements may be used for eligibility determination and baseline testing

**Visits shall continue every 6 months until the PMA order has been issued by the FDA, for device interrogation and reporting of OPTIMIZER Device related SAEs, if any Study Endpoints A primary effectiveness endpoint was an assessment of improvement from baseline in exercise tolerance at 24 weeks as measured by peak $VO_2$ obtained on cardiopulmonary exercise testing (CPX). CPX data were evaluated by an independent core laboratory. Changes in peak VO2 from baseline to 24-week follow up in subjects implanted with the 2-lead system were compared (using Bayesian statistics as detailed below) to the changes observed in control group subjects of the prior FIX-HF-5C study.

Performance of the 2-lead Optimizer system was based on an assessment of the average daily amount of Cardiac Contractility Modulation signals delivered between the 2-week visit (for device check and parameter optimization) to the end of the 24-week study period. The device has an internal counter which, among other things, keeps track of the total number of Cardiac Contractility Modulation signals delivered, and this information is readily available from device interrogation using the system programmer. The performance was specifically assessed through a comparison between the number of Cardiac Contractility Modulation signals delivered by the 2-lead device and the number of signals delivered in subjects implanted with the 3-lead system over a 24-week period in the prior FIX-HF-5C study. Additional efficacy endpoints included assessment of New York Heart Association functional class and NT-proBNP.

All-cause mortality and the composite of cardiovascular mortality and heart failure hospitalizations constituted additional safety endpoints.

Cardiopulmonary Stress Testing Procedures

As in the prior FIX-HF-5C study, rigorous quality measures and procedures were used during the conduct of CPX tests to optimize test quality and assure maximal effort was attained by each subject. All tests were reviewed by the same core laboratory employed in the prior FIX-HF-5 and FIX-HF-5C studies. Specific quality measures included:

1) on-site training on standardized procedures for conducting CPX testing;

2) normal subject validation testing and revalidation every 6 months;

3) providing the subject with instructions on how to prepare for the CPX test; and 4) rapid feedback on quality of every test from the core laboratory and retest requests for inadequate tests.

Tests were deemed inadequate if:

1) the subject had an erratic or oscillatory breathing pattern;

2) the data were non-physiologic;

3) an issue was identified with the testing equipment; or 4) the test was submaximal, meaning it was terminated by either the subject or the supervising clinician/technician prior to the subject reaching volitional exhaustion.

Reasons for early termination could include non-heart failure symptoms (e.g., angina, heart rhythm disturbance, or leg, foot, or back pain) or the subject was technically challenged to perform the test.

Metabolic data were collected for 2 minutes prior to the start of exercise to confirm RER, $VO_2$, and the subject's ventilation volume were at normal, physiologic, and stable resting values before beginning the test. Metabolic data were then collected for the duration of the test and for an additional 2-minute recovery period following termination of the test. Peak $VO_2$ and peak respiratory exchange ratio (RER) were determined by the core lab from 20 second averaged gas exchange data from the start of exercise to the end of exercise. Tests were deemed to be of maximal effort if RER reached 1.05 or greater.

Statistics

A purpose of the present study was to determine, relative to the 3-lead Optimizer system that recently received approval by the US-FDA, whether the 2-lead Optimizer Smart system performs similarly with regard to the amount of Cardiac Contractility Modulation delivered, whether the device is equally safe in terms of device- and procedure-related complications (primary safety endpoint), and whether the device provides similar clinical benefits in terms of improvements in exercise tolerance (primary efficacy endpoint) and functional class (secondary efficacy endpoint). The current study is a single arm, treatment only study. Accordingly, results from the present study were compared with data from the prior FIX-HF-5C control and treatment patients in which the 3-lead Optimizer system was used.

Baseline demographic data were summarized using descriptive statistics. Demographic data from the prior FIX-HF-5C study are also summarized here and compared to those of patients enrolled in the present study. Continuous data were compared using the two-sample t-test and categorical data were compared using Fisher's Exact test.

Efficacy: Peak VO2

Analogous to the FIX-HF-5C primary efficacy analysis plan (and with US-FDA collaboration), the FIX-HF-5C2 primary efficacy analysis plan used a Bayesian repeated measures model to estimate group differences in the change in mean peak VO2 at 24 weeks from baseline in FIX-HF-5C2 2-lead Optimizer subjects compared to FIX-HF-5C control subjects, with 30% borrowing of information (70% down-weighting) from the corresponding treatment group difference observed in the FIX-HF-5 subgroup data. The 30% borrowing was based on power-prior methodology of Ibrahim & Chen.

Efficacy: NYHA

Changes from baseline of at least one category in NYHA class were assessed and compared between groups via Fisher's Exact test. Shift tables for NYHA class in the FIX-HF-5C2 study were analyzed using the extended McNemar's test for paired data and more than 2 groups and where compared between groups via the Cochran-Mantel-Haenszel test.

Device Performance:

Device performance was assessed via an evaluation of the total number of Cardiac Contractility Modulation pulses delivered through the 24-week study follow-up period. The device was considered to perform as intended if the number of Cardiac Contractility Modulation pulse delivered was equivalent to the total number of Cardiac Contractility Modulation pulses delivered by the 3-lead system during the 24-week period of the FIX-HF-5C study. Bioequivalence was assessed by the two-sided $100(1\text{-}2\alpha)\%$ confidence interval, for the difference in the anticipated mean values of the FIX-HF-5C2 and FIX-HF-5C total Cardiac Contractility Modulation delivery, $\mu_{5C2}$-$\mu_{5C}$. The lower and upper bounds of bioequivalence were established by $\theta_L$ and $\theta_U$, where $\theta_L<0<\theta_U$, and defined as $\theta_L=-0.125\mu_{5C}$ and $\theta_U=0.125\mu_{5C}$. According to Schuirmann, bioequivalence could be conceded if the two-sided $100(1\text{-}2\alpha)\%$ confidence interval, for the difference $\mu_{5C2}-\mu_{5C}$, was completely contained within the interval $(\theta_L, \theta_U)$. Based on the estimated mean in the FIX-HF-5C study, the lower and upper bounds for bioequivalence was (−2448, 2448) Cardiac Contractility Modulation pulses/day which is calculated from the estimated mean daily rate of Cardiac Contractility Modulation delivery observed in the 5C study (19,583) as −0.125 times the estimated mean and +0.125 times the estimated mean (i.e., 19583*0.125=±2448).

Safety:

The primary safety analysis evaluated the procedure- or device-related complication rates through 24-weeks of follow up. An exact binomial 95% confidence interval for the complication free proportion was generated. These rates were compared to those observed in the FIX-HF-5C study via Fisher's Exact test.

Assessment of all-cause mortality and the composite of cardiovascular mortality and heart failure hospitalizations were explored via Kaplan-Meier analyses. Results were compared to those of the FIX-HF-5C control group via the log-rank test.

Sample Size Justification:

60 subjects were enrolled in the FIX-HF-5C2 study. Simulations were used to quantify power and Type I error of the primary efficacy analysis under a variety of assumptions and magnitude of treatment effects, in which data were prospectively simulated for both FIX-HF-5C control and FIX-HF-5C2 device patients. For instance, assuming the variance of change in peak VO2 in the FIX-HF-5C2 and FIX-HF-5C populations was equivalent to the estimated variance in the FIX-HF-5 trial, the study had approximately 80% power to detect a mean difference in peak VO2 of 0.65 mL/kg/min. The Type I error was estimated to be approximately 0.10 or less, which was deemed acceptable for the FIX-HF-5C2 trial by regulatory authorities.

Results

Subject disposition is summarized in Table 3. 153 subjects were screened at 8 sites. Of these, 60 subjects qualified and were enrolled and were implanted with the 2-lead Optimizer system. One subject withdrew from the study prior to 24 weeks due to incarceration. There were no deaths during the 24 Week study period and all remaining 59 subjects completed the final follow up visits, including assessments of Cardiac Contractility Modulation delivery and NYHA functional class. Of these, 55 subjects (91.7%) completed the 24-week CPX test. Reasons for the 4 missing tests were intervening knee replacement, knee injury, lung tumor and pulmonary embolism (one each). In addition, four 24-week CPX tests were deemed inadequate by the core lab for which the patients declined requests to repeat testing, resulting in 52 tests for the primary end-point analysis. However, to ensure robustness of findings, an additional analysis was performed that included these inadequate tests.

TABLE 3

| Subject Disposition | |
|---|---|
| Variable | FIX-HF-5C2 Optimizer |
| Screened | 153 |
| Enrolled/Implanted | 60 (39.2%) |
| Died[1] | 0 (0.0%) |
| Withdrawn[1] | 1 (1.7%) |
| 12 Week Visit Completed | 59 (98.3%) |
| 12 Week Exercise Tolerance Test Completed | 53 (88.3%) |
| 12 Week Exercise Tolerance Test Evaluable[2] | 52 (86.7%) |
| 24 Week Visit Completed | 59 (98.3%) |
| 24 Week Exercise Tolerance Test Completed | 55 (91.7%) |
| 24 Week Exercise Tolerance Test Evaluable[2] | 52 (86.7%) |

[1]Prior to 24 Week Visit
[2]Includes only subjects with valid Peak $VO_2$, as determined by the core lab, at the indicated visit.

Baseline Characteristics

Baseline characteristics of FIX-HF-5C2 subjects are presented in Table 4 along with baseline characteristics of the FIX-HF-5C study groups; as detailed above results from the prior FIX-HF-5C study are used as basis for assessment of the 2-lead Optimizer system performance (compared to FIX-HF-5C Optimizer group) and clinical effects (compared to FIX-HF-5C Control group). First, consistent with the goal of implementing the 2-lead system, 15% of FIX-HF-5C2 subjects had permanent atrial fibrillation. In addition, FIX-HF-5C2 subjects trended to be older (66.3±8.9 vs 62.8±11.4), had a lower prevalence of diabetes (30% vs. 48.8%), and had a lower LV end-diastolic dimension (57.7±6.8 vs. 60.2±7.0) than subjects in the FIX-HF-5C Control group; LVEF, however, did not differ between groups (34.1±6.1 vs. 32.5±5.2%). Baseline peak VO2 was similar between the two groups, but the FIX-HF-5C2 subjects exercised longer than the FIX-HF-5C control group subjects (11.6±2.9 vs. 10.6±3.1 minutes). All other baseline characteristics were similar between the groups. NT-proBNP (which was not recorded in the prior FIX-HF-5C study) was only minimally elevated at baseline (median (IQR): 511 (219, 867) pg/ml) and did not change significantly through the 24-week study period (median (IQR): 524 (245, 1182) pg/ml).

TABLE 4

Baseline Characteristics of the FIX-HF-5C2 population versus those of the FIX-HF-5C study

| | FIX-HF-5C2 | FIX-HF-5C | | | |
|---|---|---|---|---|---|
| Variable | Optimizer | Optimizer | P-value[1] | Control | P-value[1] |
| Age (yrs) | 66.3 ± 8.9 (60) | 63.1 ± 10.9 (74) | 0.071 | 62.8 ± 11.4 (86) | 0.049 |
| Male | 53 (88.3%) | 54 (73.0%) | 0.032 | 68 (79.1%) | 0.182 |
| Ethnicity (White) | 40 (66.7%) | 55 (74.3%) | 0.346 | 61 (70.9%) | 0.590 |
| BMI (kg/m2) | 31.4 ± 6.1 (60) | 32.5 ± 5.6 (74) | 0.267 | 32.9 ± 6.9 (86) | 0.167 |
| Resting HR (bpm) | 72.9 ± 14.4 (60) | 72.1 ± 10.9 (74) | 0.720 | 74.3 ± 13.4 (86) | 0.525 |
| Systolic Blood Pressure (mmHg) | 121.8 ± 14.6 (60) | 122.7 ± 17.7 (74) | 0.767 | 126.0 ± 18.8 (86) | 0.147 |
| Diastolic Blood Pressure (mmHg) | 74.0 ± 9.2 (60) | 73.5 ± 11.4 (74) | 0.781 | 74.2 ± 10.8 (86) | 0.940 |
| CHF Etiology (Ischemic) | 41 (68.3%) | 46 (62.2%) | 0.473 | 51 (59.3%) | 0.299 |
| Prior MI | 36 (60.0%) | 36 (48.6%) | 0.224 | 51 (59.3%) | 1.000 |
| Prior CABG | 13 (21.7%) | 18 (24.3%) | 0.837 | 23 (26.7%) | 0.560 |
| Prior ICD or PM System | 55 (91.7%) | 67 (94.4%) | 0.731 | 73 (85.9%) | 0.432 |
| Prior ICD (ICD, CRT-D, S-ICD) | 53 (88.3%) | 66 (93.0%) | 0.382 | 73 (85.9%) | 0.804 |
| Prior PM | 2 (3.3%) | 1 (1.4%) | 0.593 | 0 (0.0%) | 0.170 |
| Diabetes | 18 (30.0%) | 38 (51.4%) | 0.014 | 42 (48.8%) | 0.027 |
| Permanent Atrial Fibrillation | 9 (15.0%) | 0 (0%) | 0.0005 | 0 (0%) | 0.0002 |
| NYHA | | | | | |
| Class III | 59 (98.3%) | 64 (86.5%) | 0.023 | 78 (90.7%) | 0.082 |
| Class IV | 1 (1.7%) | 10 (13.5%) | 0.023 | 8 (9.3%) | 0.082 |
| QRS Duration (ms) | 101.2 ± 12.3 (60) | 102.5 ± 12.6 (74) | 0.555 | 103.6 ± 12.1 (86) | 0.244 |
| LVEF (%) (core lab) | 34.1 +6.1 (60) | 33.1 ± 5.5 (74) | 0.329 | 32.5 ± 5.2 (86) | 0.107 |
| LVEDD (mm) (core lab) | 57.7 ± 6.8 (57) | 58.5 ± 7.2 (74) | 0.543 | 60.2 ± 7.0 (82) | 0.040 |
| Baseline Peak VO2 (ml/kg/min) | 15.0 ± 2.9 (60) | 15.5 ± 2.6 (73) | 0.317 | 15.4 ± 2.8 (86) | 0.462 |
| Baseline RER | 1.15 ± 0.06 (60) | 1.15 ± 0.06 (73) | 0.891 | 1.14 ± 0.07 (86) | 0.500 |
| Baseline Exercise Time (minutes) | 11.6 ± 2.9 (60) | 11.4 ± 3.1 (73) | 0.662 | 10.6 ± 3.1 (86) | 0.044 |

[1]Compared to FIX-HF-5C2 Optimizer Group via Fishers exact test for binary variables and two-sample t-test for continuous variables.

FIX-HF-5C2 subjects were receiving guideline-recommended medical therapy (Supplemental Table 1) that were similar to the FIX-HF-5C subjects except for greater use of combined angiotensin receptor/neprilysin inhibitor (ARNi) and anti-arrhythmic agents (mainly amiodarone); increased ARNi use is due to the later start date of the study, while antiarrhythmic use was due to the higher prevalence of atrial fibrillation.

SUPPLEMENTAL TABLE 1

Baseline Heart Failure Medications in FIX-HF-5C2 and FIX-HG-5C populations

| | FIX-HF-5C2 | FIX-HF-5C | | | |
|---|---|---|---|---|---|
| Variable | Optimizer | Optimizer | P-value[1] | Control | P-value[1] |
| ACEi/ARB/ARNi | 45 (75.0%) | 61 (82.4%) | 0.393 | 72 (83.7%) | 0.212 |
| ACE inhibitor | 29 (48.3%) | 40 (54.1%) | 0.603 | 49 (57.0%) | 0.317 |
| ARB | 8 (13.3%) | 18 (24.3%) | 0.128 | 22 (25.6%) | 0.096 |
| ARNi | 9 (15.0%) | 3 (4.1%) | 0.035 | 3 (3.5%) | 0.028 |
| Beta Blocker | 57 (95.0%) | 72 (97.3%) | 0.656 | 82 (95.3%) | 1.000 |
| Diuretic | 44 (73.3%) | 57 (77.0%) | 0.689 | 67 (77.9%) | 0.558 |
| Secondary Diuretic | 5 (8.3%) | 6 (8.1%) | 1.000 | 8 (9.3%) | 1.000 |
| Ivabradine | 3 (5.0%) | 2 (2.7%) | 0.656 | 4 (4.7%) | 1.000 |
| Digoxin | 4 (6.7%) | 10 (13.5%) | 0.260 | 8 (9.3%) | 0.762 |
| Aldosterone Inhibitor | 25 (41.7%) | 26 (35.1%) | 0.477 | 33 (38.4%) | 0.733 |
| Hydralazine | 3 (5.0%) | 5 (6.8%) | 0.731 | 10 (11.6%) | 0.240 |
| Nitrates | 11 (18.3%) | 18 (24.3%) | 0.527 | 26 (30.2%) | 0.124 |
| Anti-arrhythmic | 19 (31.7%) | 14 (18.9%) | 0.108 | 12 (14.0%) | 0.013 |

[1]Compared to FIX-HF-5C2 Optimizer Group via Fishers exact test.

The study protocol stipulated that medical therapy was to remain constant unless mandated by clinical care considerations. The numbers of medication adjustments between baseline and 24 weeks are detailed in Supplemental Table 2. For each drug class, the number of instances of dose increases was balanced by the number of dose decreases; for this analysis, any increase or decrease of dose was counted. There were 2 cases where angiotensin receptor blockers were switched to sacubitril/valsartan and one case of an opposite switch.

SUPPLEMENTAL TABLE 2

Number of dose increases and decreases by drug class.

| Drug Class | Decreases | Increases |
|---|---|---|
| ACEi or ARB | 4 | 6 |
| β-Blocker | 6 | 12 |
| Diuretic | 9 | 8 |
| 2nd Diuretic* | 5 | 5 |
| ARNi | 1 | 1 |
| ABR/ARNi Switch | ARNi-->ARB | ARB-->ARNi |
| | 1 | 2 |

Abbreviations: ACEi, angiotensin converting enzyme inhibitor; ABR, angiotensin receptor blocker; ARNi, combined angiotensin receptor/neprilysin inhibitor.

Device Performance

The average daily number of Cardiac Contractility Modulation pulses delivered during the 24-week study period is summarized in Table 5. The devices were programmed to deliver Cardiac Contractility Modulation therapy 5 hours per day, delivered evenly across each 24-hour period. Assuming an average heart rate of 72 bpm (from Table 4), the expected daily number of beats eligible for Cardiac Contractility Modulation signal delivery is 21,600. As summarized in Table 5, the average daily number of beats was just under 20,000 (95% of predicted), and this did not differ significantly between the FIX-HF-5C (3-lead system) and FIX-HF-5C2 (2-lead system) studies. Based on formal statistical testing detailed in Methods, the total Cardiac Contractility Modulation delivery at 24 weeks is equivalent between the 2-lead (FIX-HF-5C2 study) and 3-lead (FIX-HF-5C study) Optimizer systems since the 95% confidence interval of the difference between the 2 groups lies wholly within the interval $\Theta_L$, $\Theta_U$ (i.e., −2448,2448). Also, importantly, as detailed in Table 5, the amount of Cardiac Contractility Modulation signal delivery did not differ significantly between subjects with or without permanent atrial fibrillation.

TABLE 5

Number of Cardiac Contractility Modulation signals delivered in 24 weeks; comparison between 2- and 3-lead systems, with and without permanent atrial fibrillation.

| Cardiac Contractility | FIX-HF-5C2 | | | | |
|---|---|---|---|---|---|
| Modulation Signal Delivery | All (n = 59) | NSR (n = 50) | Atrial Fibrillation (n=9) | FIX-HF-5C NSR (n = 67) | Difference* |
| Mean ± SD | 19892 ± 3472 | 19921 ± 3377 | 19734 ± 4187 | 19583 ± 4998 | 310 ± 4352 |
| (min, max) | (11618, 28284) | (11618, 28284) | (12787, 24578) | (3645, 31009) | |
| [95% CI] | [18988, 20797] | [18961, 20881] | [16515, 22952] | [18364, 20802] | [−1228, 1847] |

Figures 1A, 1B:
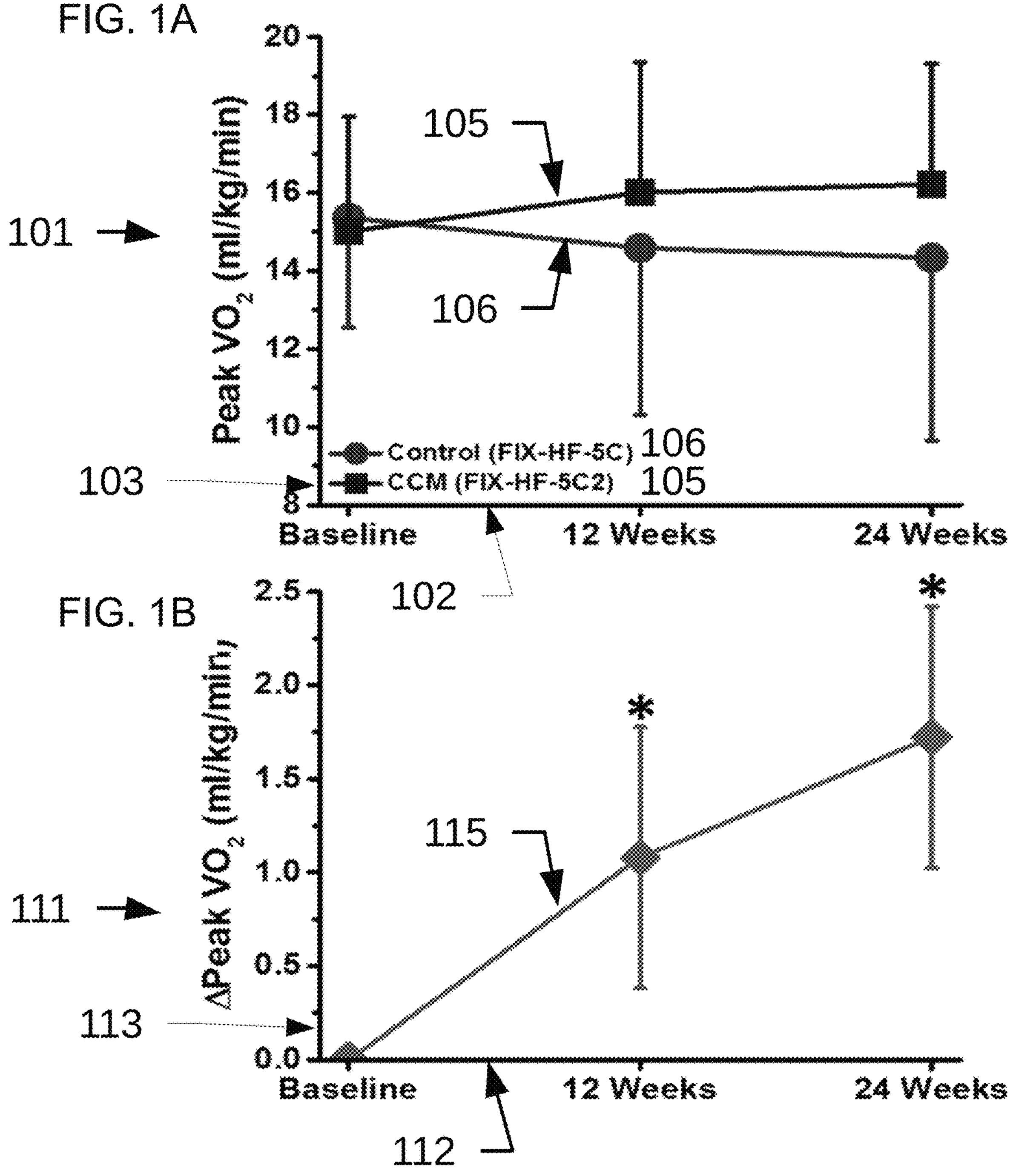
FIG. 1A shows a graph of Peak VO2 over time comparing the control group from FIX-HF-5C and the Cardiac Contractility Modulation treatment group from the FIX-HF-5C2 study according to an example embodiment of the invention.
FIG. 1B shows a graph of Between-group treatment effects (difference between Cardiac Contractility Modulation treatment and control group) over time according to an example embodiment of the invention.

*Difference between all patients of FIX-HF-5C2 and Cardiac Contractility Modulation-treated patients of FIX-HF-5C Peak $VO_2$ Baseline peak $VO_2$ was similar between FIX-HF-5C2 2-lead Optimizer patients and FIX-HF-5C control patients at baseline (FIG. 1A). As detailed above, follow-up results for the primary analysis were available from 52 of these subjects. Peak VO2 increased progressively over time in the 2-lead Optimizer group (by 0.80 ml/kg/min from baseline to 24 weeks) but declined in the FIX-HF-5C control group (by 0.93 ml/kg/min from baseline to 24 weeks). The primary endpoint, a Bayesian analysis of the difference between groups (FIG. 1B) was 1.08 (95% Bayesian Credible Interval [BCI]:0.38, 1.78) ml/kg/min at 12 weeks and this increased to 1.72 (95% BCI: 1.02, 2.42) ml/kg/min by 24 weeks, both of which were highly statistically significant (Bayesian posterior probability of superiority equals 1.00). Thus, exercise tolerance improved in response to Cardiac Contractility Modulation treatment provided by the 2-lead Optimizer system relative to FIX-HF-5C control patients.

Reference is now made to FIG. 1A, which shows a graph of Peak $VO_2$ over time comparing the control group from FIX-HF-5C and the Cardiac Contractility Modulation treatment group from the FIX-HF-5C2 study according to an example embodiment of the invention.

FIG. 1A shows a graph 101 having an X-axis of time in weeks, and a Y-axis showing peak VO2 in units of ml/kg/min.

The graph 101 shows a first line 106, showing Peak VO2 over time from the control group from FIX-HF-5C, and a second line 105 showing Peak VO2 over time from the Cardiac Contractility Modulation treatment group from the FIX-HF-5C2 study.

The bars above and below the data points on the graph indicate a statistical estimate of the error of the data values, based on the individual data and the population size of the experiments.

Reference is now made to FIG. 1B, which shows a graph of between-group treatment effects (difference between Cardiac Contractility Modulation treatment and control group) over time according to an example embodiment of the invention.

FIG. 1B shows a graph 111 having an X-axis of time in weeks, and a Y-axis showing differences (Δ) in peak VO2 between the groups in units of ml/kg/min.

The graph 11 shows a line 115, showing a difference between the groups over time, where the difference is positive when the peak VO2 of the Cardiac Contractility Modulation group is larger than the peak VO2 of the control group.

Sensitivity analyses were conducted for the primary analysis, that included a Bayesian analysis with covariate adjustment for heart failure etiology and baseline ejection fraction. In all cases, the posterior probability for superiority of the 2-lead Optimizer system versus FIX-HF-5C control patients was 1.00, exceeding the threshold of 0.975 required to demonstrate superiority. In addition, a supporting non-Bayesian (frequentist) estimate of benefit without 30% borrowing from FIX-HF-5 data was comparable (2.21 mL/kg/min) with a p-value<0.001, indicating that borrowing was not necessary to achieve statistical significance with respect to the primary efficacy endpoint. Finally, upon inclusion of the 4 inadequate CPX tests, the frequentist estimate of the benefit was 2.09 ml/kg/min (p<0.001).

Additional analysis showed that respiratory exchange ratios (RERs, index of subject effort) were similar between 2-lead Optimizer and FIX-HF-5C control subjects both at baseline (1.15±0.06 vs 1.14±0.07, p=0.50) and at 24 weeks (1.16±0.04 vs 1.16±0.07, p=0.96). Finally, the duration of exercise increased from baseline to 24 weeks by 1.31±2.08 min in Cardiac Contractility Modulation-treated subjects with the 2-lead Optimizer system, compared with a 0.60±2.31 min in FIX-HF-5C control subjects.

NYHA

NYHA improved by at least 1 functional class in 83.1% of subjects treated with the 2-lead Optimizer system at 24 weeks compared to only 42.7% in the FIX-HF-5C control group (p<0.001). Comparisons of NYHA distributions between 2-lead Optimizer and FIX-HF-5C controls groups are summarized in FIGS. 2A and 2B, respectively.

Reference is now made to FIGS. 2A and 2B, which are graphs of New York Heart Association (NYHA) Functional Classification Distributions at baseline versus 24 weeks in the control group and in the 2-lead Optimizer group.

FIG. 2A shows a graph 201 having an X-axis 202 of NYHA functional classes, and a Y-axis 203 showing percent of patients in the control group.

FIG. 2A shows the NYHA functional classes of the control group at the baseline 205 and the NYHA functional classes of the control group at the 24 week time 206.

FIG. 2B shows a graph 211 having an X-axis 212 of NYHA functional classes, and a Y-axis 213 showing percent of patients in the 2-lead Optimizer group.

FIG. 2B shows the NYHA functional classes of the 2-lead Optimizer group at the baseline 215 and the NYHA functional classes of the 2-lead Optimizer group at the 24 week time 216.

As illustrated, there was a greater shift toward lower NYHA in the 2-lead Optimizer group than in the FIX-HF-5C control group (p<0.001).

Primary Safety Endpoint Analysis

The primary safety endpoint was the composite of the percentage of subjects in the 2-lead Optimizer group who experienced an Optimizer device- or procedure-related complication through the 24-week follow-up period as determined by the EAC. There was only 1 complication observed, which was a hematoma at the Optimizer implant site requiring the patient to remain in the hospital overnight for observation. The hematoma resolved without treatment and there were no further complications in this case. Thus, the complication rate was 1.7% (1/60; confidence interval 0.0%, 8.9%). This compares with the 10.3% complication rate seen in 3-lead Optimizer subjects in the FIX-HF-5C study (p=0.07; confidence interval 4.2%, 20.1%).

Secondary Safety Endpoints

As noted above, there were no deaths during the 24-week study period in the 2-lead Optimizer subjects; in contrast there were 4 deaths in the FIX-HF-SC control subjects during the same period of follow up. Serious adverse events were tabulated by treatment group and were compared by Fisher's exact test (Table 6). There were no significant differences between the 2-lead Optimizer (FIX-HF-5C2) subjects and FIX-HF-5C Control or 3-lead Optimizer (FIX-HF-5C) subjects with the exception that there were fewer Optimizer device-related events with the 2-lead system (p=0.03). It is notable that a majority of the Optimizer device-related events with the prior FIX-HF-5C 3-lead system study were due to lead dislodgements and lead fractures; there were no device-related complications reported with the 2-lead device. Importantly, there were no occurrences of premature ventricular contractions or ventricular tachycardia events in the FIX-HF-5C2 study.

TABLE 6

Adjudicated Serious Adverse Events from study day 0-168

| | FIX-HF-SC2 Optimizer | | FIX-HF-5C Optimizer | | | FIX-HF-5C Control | | |
|---|---|---|---|---|---|---|---|---|
| Variable | # Events | # and % of Subjects[2] (CI) | # Events | # and % of Subjects[2] (CI) | P-value[1] | # Events | # and % of Subjects[2] (CI) | P-value[1] |
| All | 26 | 19 (31.7%) (20.3%, 45.0%) | 29 | 20 (27.0%) (17.4%, 38.6%) | 0.572 | 27 | 19 (22.1%) (13.9%, 32.3%) | 0.250 |
| General Medical | 8 | 7 (11.7%) (4.8%, 22.6%) | 7 | 7 (9.5%) (3.9%, 18.5%) | 0.779 | 8 | 7 (8.1%) (3.3%, 16.1%) | 0.571 |
| Arrhythmia | 3 | 2 (3.3%) (0.4%, 11.5%) | 3 | 3 (4.1%) (0.8%, 11.4%) | 1.000 | 2 | 2 (2.3%) (0.3%, 8.1%) | 1.000 |
| Worsening Heart Failure | 7 | 5 (8.3%) (2.8%, 18.4%) | 4 | 3 (4.1%) (0.8%, 11.4%) | 0.466 | 8 | 7 (8.1%) (3.3%, 16.1%) | 1.000 |
| General Cardiopulmonary | 2 | 2 (3.3%) (0.4%, 11.5%) | 4 | 3 (4.1%) (0.8%, 11.4%) | 1.000 | 2 | 2 (2.3%) (0.3%, 8.1%) | 1.000 |
| Bleeding | 1 | 1 (1.7%) (0.0%, 8.9%) | 0 | 0 (0.0%) (0.0%, 4.9%) | 0.448 | 1 | 1 (1.2%) (0.0%, 6.3%) | 1.000 |
| Neurologic | 1 | 1 (1.7%) (0.0%, 8.9%) | 0 | 0 (0.0%) (0.0%, 4.9%) | 0.448 | 0 | 0 (0.0%) (0.0%, 4.2%) | 0.411 |
| Thromboembolism | 1 | 1 (1.7%) (0.0%, 8.9%) | 1 | 1 (1.4%) (0.0%, 7.3%) | 1.000 | 1 | 1 (1.2%) (0.0%, 6.3%) | 1.000 |
| Local Infection | 1 | 1 (1.7%) (0.0%, 8.9%) | 1 | 1 (1.4%) (0.0%, 7.3%) | 1.000 | 4 | 4 (4.7%) (1.3%, 11.5%) | 0.649 |
| Sepsis | 1 | 1 (1.7%) (0.0%, 8.9%) | 1 | 1 (1.4%) (0.0%, 7.3%) | 1.000 | 1 | 1 (1.2%) (0.0%, 6.3%) | 1.000 |
| ICD or Pacemaker System Malfunction | 1 | 1 (1.7%) (0.0%, 8.9%) | 2 | 2 (2.7%) (0.3%, 9.4%) | 1.000 | 0 | 0 (0.0%) (0.0%, 4.2%) | 0.411 |
| OPTIMIZER System Malfunction | 0 | 0 (0.0%) (0.0%, 6.0%) | 6 | 6 (8.1%) (3.0%, 16.8%) | 0.033 | | — | |

[1]Compared to FIX-HF-5C2 Optimizer Group via Fishers exact test.

[2]Number and percent of subjects. Subjects are counted only once within each category.

Discussion

The present results demonstrate that compared to the prior 3-lead system, the 2-lead Optimizer Smart device delivers equivalent amounts of Cardiac Contractility Modulation treatment and device-related events are decreased, presumably related to having 1 less lead. Compared to the results of the prior FIX-HF-5C study, the improvements in peak VO2 and NYHA appear to be equivalent (or greater) with the 2-lead system. In addition, device performance did not differ between patients with normal sinus rhythm or atrial fibrillation. As such, the present study represents a significant advance for patients who qualify for Cardiac Contractility Modulation treatment and potentially expands the eligible pool of patients to those with permanent atrial fibrillation.

The prior Optimizer system required an atrial lead for sensing of a p wave, the timing of which relative to the depolarizations at the two RV septal leads, was part of the algorithm that ensured Cardiac Contractility Modulation signal delivery during the myocardial absolute refractory period. Elimination of the atrial lead was made through modifying the algorithm to eliminate the atrio-ventricular timing criteria, while at the same time strengthening criteria used to evaluate the timing and sequence between the two RV leads. In addition to prior significant benchtop and pre-clinical testing of that algorithm, the present results indicating no occurrences of premature ventricular contractions or ventricular tachycardia events in the FIX-HF-5C2 provides important additional safety information.

The Bayesian model-based mean change in peak VO2 from baseline to 24 weeks in the FIX-HF-5C2 study increased by 0.80 (95% BCI: 0.18,1.40) ml/kg/min, whereas the model-based mean change in peak $VO_2$ from baseline to 24 weeks in the FIX-HF-5C control group decreased by 0.93 (95% BCI: −1.46, −0.39). The corresponding treatment effect (i.e., the Bayesian primary analysis model-based mean difference in peak $VO_2$ change at 24-weeks between the FIX-HF-5C2 treatment group and the FIX-HF-5C control group) was 1.72 (95% BCI: 1.02, 2.42) ml/kg/min. This was supported by a frequentist analysis (i.e., no borrowing) which showed a 2.21 ml/kg/min Cardiac Contractility Modulation treatment effect. This effect is near the upper bound of the Bayesian model-based mean treatment effect identified in the prior FIX-HF-SC study: 0.84 ml/kg/min (95% BCI: 0.12, 1.52). The larger mean treatment effect identified in the present study is due to the fact that peak $VO_2$ in the FIX-HF-5C2 patients increased significantly over baseline at 24 weeks, whereas there was almost no change from baseline in the FIX-HF-5C Cardiac Contractility Modulation patients. It can only be speculated as to why the treatment group appeared to have behaved differently in the FIX-HF-5C and FIX-HF-5C2 studies. Placebo effect is unlikely since both studies were unblinded and the same core lab oversight was applied in both studies. One difference between studies was that in FIX-HF-5C, patients underwent 2 CPX tests at each time point in addition to a 6-minute walk test; in FIX-HF-5C2, only one CPX test was performed at each time point and there was no 6-minute walk test. This methodological difference could have influenced patient performance on serial tests; results in the FIX-HF-5C2 could have been more reflective of habituation on repeated tests, whereas the more frequent exercise testing used in the FIX-HF-5C study could have blunted this effect. Nevertheless, the less frequent CPX testing schedule used in the FIX-HF-5C2 study is more reflective of how patients are evaluated serially in clinical practice and in most prior clinical trials.

Limitations

A potential limitation of the present study is that it was a nonrandomized, unblinded study that used a historical control group from the prior FIX-HF-5C study. The two studies are reasonably contemporaneous, having been completed less than 2 years of each other. The only significant difference in background medical therapy was a slightly greater use of valsartan/sacubitril in the current study (15% vs 4%) due to its introduction into clinical practice towards the completion of enrollment into the FIX-HF-5C study. Regarding unblinding, this aspect is similar to the prior FIX-HF-5C study so we consider it unlikely that it would have influenced the comparisons made between the two studies.

Some Conclusions

The 2-Lead Optimizer Smart system potentially reduces the total lead requirement from 3-leads to 2-leads and enables Cardiac Contractility Modulation signal delivery in patients with atrial arrhythmias. Compared to the 3-lead system, the 2-lead system delivers comparable amount of Cardiac Contractility Modulation pulses, is equally safe and improves peak $VO_2$ and NYHA functional class. Device-related adverse effects related to leads are less with than the 3-lead system. The availability of the 2-lead system therefore represents a significant advance in the development of cardiac contractility modulation therapy for patients with heart failure.

It is expected that during the life of a patent maturing from this application many relevant Cardiac Contractility Modulation devices will be developed and the scope of the term Cardiac Contractility Modulation device is intended to include all such new technologies a priori.

The terms "comprising", "including", "having" and their conjugates mean "including but not limited to".

The term "consisting of" is intended to mean "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a unit" or "at least one unit" may include a plurality of units, including combinations thereof.

The words "example" and "exemplary" are used herein to mean "serving as an example, instance or illustration". Any embodiment described as an "example or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers there between.

Unless otherwise indicated, numbers used herein and any number ranges based thereon are approximations within the accuracy of reasonable measurement and rounding errors as understood by persons skilled in the art.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method of increasing peak VO2 comprising:

selecting a patient having impaired peak VO2 and the patient not known to have a medical condition which may prevent increasing peak VO2 and estimated, based on pulmonary assessment, to have a potential for improving peak VO2; wherein the selecting comprises selecting a patient estimated to have a pulmonary reserve suitable to achieve an increase in peak VO2 in response to cardiac contractility modulation stimulation; and applying cardiac contractility modulation stimulation to the patient's heart.

2. The method of claim 1, wherein the selecting comprises selecting a patient who already has an implant suitable for providing Cardiac Contractility Modulation treatment.

3. The method of claim 1, wherein the selecting the patient comprises selecting a patient with a NYHA class selected from a group consisting of:

NYHA class II;

NYHA class III; and

NYHA class IVa.

4. The method of claim 1, wherein the selecting the patient comprises selecting a patient with at least one pulmonary status selected from a group consisting of:

a Breathing Reserve (BR) above 30%;

an Oxygen Uptake Efficiency Slope (OUES) below 90%;

a peak RER above 1.05;

VE/VCO2 ratio above 30; and $O_2$ saturation falling less than 10% over a period of 20 minutes of exercise.

5. The method of claim 1, wherein the selecting the patient comprises selecting a patient with an ejection fraction above 35% and below 45%.

6. The method of claim 1, wherein the selecting the patient comprises selecting a patient with heart failure.

7. The method of claim 1, wherein the selecting the patient comprises selecting a patient with at least one condition selected from a group consisting of:

atrial fibrillation (AF);

Systolic heart failure (HF);

Diastolic HF;

Atrial Tachycardia;

Angina;

Myocarditis;

Small vessel disease;

Pulmonary hypertension;

Chronic Obstructive Pulmonary Disease (COPD); and

Sleep Apnea.

8. The method of claim 1, wherein the selecting the patient comprises selecting a patient having impaired peak VO2 and not known to have another medical condition which may limit increasing peak VO2 comprises selecting a patient which is not known to have a condition selected from a group consisting of:

a limitation in pulmonary intake of oxygen;

lung disease;

a limitation in blood flow; and peripheral blood vessel disease.

9. The method of claim 1, and further comprising detecting an improper beat when a difference between a first ventricle lead detecting ventricle contraction and a second ventricle lead detecting ventricle contraction is greater than 30 milliseconds, and not planning Cardiac Contractility Modulation stimulation application.

10. The method of claim 1, wherein the applying Cardiac Contractility Modulation stimulation to the patient's heart comprises using one or more leads placed at locations selected from a group consisting of:

the ventricular septum;

the right ventricle;

the left ventricle one location in the right ventricle and one location in the left ventricle.

11. The method of claim 1, and further comprising implanting a Cardiac Contractility Modulation device and leads in the selected patient.

12. The method of claim 1, and further comprising detecting an improper beat when a difference between a first ventricle lead detecting ventricle contraction and a second ventricle lead detecting ventricle contraction is greater than 30 milliseconds, and blocking Cardiac Contractility Modulation stimulation application.

13. A method of increasing peak VO2 comprising:

receiving by a Cardiac Contractility Modulation device said one or more treatment plans to increase peak VO2 in a patient having impaired peak VO2; wherein said one or more treatment plans takes into account one or more parameters of the patient comprising a level of pulmonary reserve;

detecting ventricle contraction using one or more leads in the patient's ventricle; and applying Cardiac Contractility Modulation stimulation to the patient's ventricle, according to said one or more treatment plans, during a ventricle refractory period, thereby increasing the patient's peak VO2.

14. The method of claim 13, wherein the applying Cardiac Contractility Modulation stimulation to the patient's heart comprises applying Cardiac Contractility Modulation stimulation to the patient's heart even during atrial fibrillation (AF).

15. A method of planning Cardiac Contractility Modulation treatment for a patient to increase peak VO2, the method comprising:

selecting a patient having impaired peak VO2 and estimated, based on pulmonary assessment, to have a potential for improving peak VO2; and planning Cardiac Contractility Modulation Treatment for the patient.

16. A Cardiac Contractility Modulation device comprising:

a controller;

at least one sensor input coupled to the controller; and a memory coupled to the controller, wherein the memory comprises instructions that, when executed by the controller, cause the controller to decide, based on the sensor input, to increase peak VO2 by providing cardiac contractility modulation stimulation to the patient's heart;

wherein the patient has impaired peak VO2 and has pulmonary reserve suitable to achieve an increase in peak VO2 in response to cardiac contractility modulation stimulation.

* * * * *